(12) United States Patent
Ryu et al.

(10) Patent No.: US 9,913,763 B2
(45) Date of Patent: Mar. 13, 2018

(54) ABSORBENT ARTICLE WITH CHANNELS

(71) Applicant: Kimberly-Clark Worldwide, Inc., Neenah, WI (US)

(72) Inventors: JinHo Ryu, Yongin-si (KR); KyoungRock Kim, Sungnam-si (KR); SeungKeun Park, Yongin-si (KR); SooYong Cho, Sungnam-si (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 15/502,847

(22) PCT Filed: Oct. 30, 2015

(86) PCT No.: PCT/US2015/058324
§ 371 (c)(1),
(2) Date: Feb. 9, 2017

(87) PCT Pub. No.: WO2017/074422
PCT Pub. Date: May 4, 2017

(65) Prior Publication Data
US 2017/0246047 A1    Aug. 31, 2017

(51) Int. Cl.
 *A61F 13/494* (2006.01)
 *A61F 13/49* (2006.01)
 (Continued)

(52) U.S. Cl.
 CPC .. *A61F 13/49001* (2013.01); *A61F 13/15747* (2013.01); *A61F 13/491* (2013.01);
 (Continued)

(58) Field of Classification Search
 CPC .......... A61F 13/49017; A61F 13/49019; A61F 2013/49031; A61F 2013/49025; A61F 2013/49034; A61F 2013/4948
 (Continued)

(56) References Cited

U.S. PATENT DOCUMENTS 3,559,648 A    2/1971  Mason, Jr.
3,575,174 A    4/1971  Mogor
(Continued)

FOREIGN PATENT DOCUMENTS

EP    1106152 A1    6/2001
EP    1447066 B1    10/2008
(Continued)

*Primary Examiner* — Susan Su
(74) *Attorney, Agent, or Firm* — Kimberly-Clark Worldwide, Inc.

(57) ABSTRACT

A personal care absorbent article is disclosed which employs a combination of void spaces, also referred to as channels, in the crotch region of the article in conjunction with shaping elastic members located outside the lateral side edges of the absorbent core, that, when coupled with strategic alignment of certain components and specifically-located folding lines, will create an article with improved convex or outward curvature of the chassis upon unfolding which provides increased spatial separation of the topsheet or body side liner of the article from the genital area of the wearer. In addition, due to the manipulation of the specific location of such elements in the article, gender specific product designs can be created which are specifically tailored to more appropriately deal with the differences in location of the male and female genitalia.

20 Claims, 16 Drawing Sheets

(51) Int. Cl.
*A61F 13/15* (2006.01)
*A61F 13/496* (2006.01)
*A61F 13/491* (2006.01)
*A61F 13/53* (2006.01)
*A61F 13/511* (2006.01)

(52) U.S. Cl.
CPC ...... *A61F 13/496* (2013.01); *A61F 13/49406* (2013.01); *A61F 13/51108* (2013.01); *A61F 13/53* (2013.01); *A61F 2013/49088* (2013.01)

(58) Field of Classification Search
USPC .............................................. 604/358–392
See application file for complete search history.

(56) References Cited

U.S. PATENT DOCUMENTS

| | | | |
|---|---|---|---|
| 4,027,672 A | 6/1977 | Karami | |
| 4,342,314 A | 8/1982 | Radel et al. | |
| 4,610,678 A | 9/1986 | Weisman et al. | |
| 4,631,062 A | 12/1986 | Schultz et al. | |
| 4,655,759 A | 4/1987 | Romans-Hess et al. | |
| 4,657,539 A | 4/1987 | Hasse | |
| 4,743,246 A | 5/1988 | Lawson | |
| 4,798,603 A | 1/1989 | Meyer et al. | |
| 4,950,263 A | 8/1990 | Lewis | |
| 5,019,070 A | 5/1991 | Ruben | |
| 5,037,413 A | 8/1991 | Haque | |
| 5,176,672 A | 1/1993 | Bruemmer et al. | |
| 5,300,053 A | 4/1994 | Genaro | |
| 5,366,453 A | 11/1994 | Zehner et al. | |
| 5,382,246 A | 1/1995 | Kawano | |
| 5,425,725 A | 6/1995 | Tanzer et al. | |
| 5,451,442 A | 9/1995 | Pieniak et al. | |
| 5,464,402 A | 11/1995 | Zajaczkowski | |
| 5,562,650 A * | 10/1996 | Everett | A61F 13/15203 604/358 |
| 5,593,399 A | 1/1997 | Tanzer et al. | |
| 5,776,122 A | 7/1998 | Faulks et al. | |
| 5,810,799 A | 9/1998 | Slater | |
| 5,817,271 A | 10/1998 | Congleton et al. | |
| 5,830,202 A | 11/1998 | Bogdanski et al. | |
| 5,849,002 A | 12/1998 | Carlos et al. | |
| 5,895,382 A | 4/1999 | Popp et al. | |
| 5,911,713 A * | 6/1999 | Yamada | A61F 13/49009 604/385.29 |
| 6,060,636 A | 5/2000 | Yahiaoui et al. | |
| 6,099,515 A | 8/2000 | Sugito | |
| 6,102,892 A | 8/2000 | Putzer et al. | |
| 6,159,190 A | 12/2000 | Tanaka et al. | |
| 6,222,092 B1 | 4/2001 | Hansen et al. | |
| 6,293,933 B1 | 9/2001 | Ahlstrand | |
| 6,315,766 B1 | 11/2001 | Drevik | |
| 6,326,525 B1 | 12/2001 | Hamajima et al. | |
| 6,328,724 B1 | 12/2001 | Ronnberg et al. | |
| 6,398,770 B1 | 6/2002 | Drevik | |
| 6,410,822 B1 | 6/2002 | Mizutani | |
| 6,436,079 B1 | 8/2002 | Blenke et al. | |
| 6,492,574 B1 | 12/2002 | Chen et al. | |
| 6,563,013 B1 | 5/2003 | Murota | |
| 6,610,903 B1 | 8/2003 | Latimer et al. | |
| 6,695,827 B2 | 2/2004 | Chen et al. | |
| 6,717,029 B2 | 4/2004 | Baker | |
| 6,852,101 B2 | 2/2005 | Damaghi et al. | |
| 6,878,139 B2 | 4/2005 | Koyama et al. | |
| 7,067,711 B2 | 6/2006 | Kuroda et al. | |
| 7,156,830 B2 | 1/2007 | Koyama et al. | |
| 7,264,614 B2 | 9/2007 | Minato | |
| 7,358,282 B2 | 4/2008 | Krueger et al. | |
| 7,442,188 B2 | 10/2008 | Franklin et al. | |
| 7,520,874 B2 | 4/2009 | Koyama et al. | |
| 7,767,878 B2 | 8/2010 | Suzuki | |
| 7,789,867 B2 | 9/2010 | Carstens | |
| 7,824,389 B2 | 11/2010 | Veith | |
| 7,879,017 B1 * | 2/2011 | Tabata | A61F 13/49017 604/385.23 |
| 7,972,316 B2 | 7/2011 | Toyoshima et al. | |
| 8,057,457 B2 | 11/2011 | Baeck et al. | |
| 8,361,047 B2 | 1/2013 | Mukai et al. | |
| 8,604,270 B2 | 12/2013 | Venturino et al. | |
| 8,633,347 B2 | 1/2014 | Bianco et al. | |
| 8,672,912 B2 | 3/2014 | Corneliusson et al. | |
| 8,771,250 B2 | 7/2014 | Carbonari | |
| 8,791,318 B2 | 7/2014 | Becker et al. | |
| 8,952,212 B2 | 2/2015 | Bissah et al. | |
| 9,044,359 B2 | 6/2015 | Wciorka et al. | |
| 2002/0065498 A1 | 5/2002 | Ohashi et al. | |
| 2004/0002690 A1 * | 1/2004 | Miyamoto | A61F 13/49017 604/385.25 |
| 2005/0148258 A1 | 7/2005 | Chakravarty et al. | |
| 2005/0256758 A1 | 11/2005 | Sierra et al. | |
| 2006/0004334 A1 | 1/2006 | Schlinz et al. | |
| 2006/0122573 A1 | 6/2006 | Terada et al. | |
| 2006/0282055 A1 | 12/2006 | Shiomi et al. | |
| 2007/0078422 A1 | 4/2007 | Glaug et al. | |
| 2007/0244455 A1 | 10/2007 | Hansson et al. | |
| 2008/0021427 A1 | 1/2008 | Iwao | |
| 2008/0312631 A1 * | 12/2008 | Okuda | A61F 13/15699 604/385.23 |
| 2009/0112175 A1 | 4/2009 | Bissah et al. | |
| 2009/0240229 A1 * | 9/2009 | Malowaniec | A61F 13/49017 604/385.28 |
| 2009/0270825 A1 | 10/2009 | Wciorka et al. | |
| 2010/0174260 A1 | 7/2010 | Di Luccio et al. | |
| 2010/0318053 A1 * | 12/2010 | Smet | A61F 13/49019 604/385.23 |
| 2012/0035573 A1 * | 2/2012 | Kuwano | A61F 13/49011 604/385.16 |
| 2012/0143162 A1 | 6/2012 | Mukai et al. | |
| 2012/0150135 A1 * | 6/2012 | Tee, Jr. | A61F 13/4753 604/372 |
| 2012/0220972 A1 | 8/2012 | Kawamura et al. | |
| 2012/0316526 A1 | 12/2012 | Rosati et al. | |
| 2012/0316528 A1 | 12/2012 | Kreuzer et al. | |
| 2012/0323206 A1 * | 12/2012 | McMorrow | A61F 13/49413 604/385.24 |
| 2013/0030398 A1 | 1/2013 | Arayama et al. | |
| 2013/0030402 A1 | 1/2013 | Arayama et al. | |
| 2013/0041336 A1 | 2/2013 | Mukai et al. | |
| 2013/0211354 A1 * | 8/2013 | Tsuji | A61F 13/42 604/361 |
| 2013/0211355 A1 | 8/2013 | Nishikawa et al. | |
| 2013/0226120 A1 | 8/2013 | Van De Maele | |
| 2013/0267924 A1 | 10/2013 | Mukai et al. | |
| 2013/0289509 A1 | 10/2013 | Mukai et al. | |
| 2014/0163501 A1 | 6/2014 | Ehrnsperger et al. | |
| 2014/0163506 A1 | 6/2014 | Roe et al. | |
| 2014/0163509 A1 * | 6/2014 | Gassner | A61F 13/49061 604/385.16 |
| 2014/0188066 A1 | 7/2014 | Mukai et al. | |
| 2014/0276511 A1 | 9/2014 | Bauduin et al. | |
| 2014/0303583 A1 * | 10/2014 | Berrizbeitia | A61F 13/4942 604/365 |
| 2014/0336608 A1 | 11/2014 | Hao et al. | |
| 2014/0338822 A1 | 11/2014 | Mukai et al. | |
| 2014/0350504 A1 | 11/2014 | Popp et al. | |
| 2014/0371701 A1 | 12/2014 | Bianchi et al. | |
| 2015/0038931 A1 | 2/2015 | Kreuzer et al. | |
| 2015/0065973 A1 | 3/2015 | Roe et al. | |
| 2015/0065975 A1 | 3/2015 | Roe et al. | |
| 2015/0065976 A1 | 3/2015 | Roe et al. | |
| 2015/0073366 A1 | 3/2015 | Ehmsperger et al. | |
| 2015/0080828 A1 * | 3/2015 | Suzuki | A61F 13/4942 604/385.01 |
| 2015/0100036 A1 * | 4/2015 | Sakaguchi | A61F 13/534 604/385.03 |
| 2015/0283000 A1 | 10/2015 | Faulks et al. | |
| 2015/0366724 A1 * | 12/2015 | Fukuzawa | A61F 13/496 604/385.01 |
| 2015/0374559 A1 * | 12/2015 | Fukuzawa | A61F 13/49011 604/385.29 |

(56) References Cited

U.S. PATENT DOCUMENTS

| | | | |
|---|---|---|---|
| 2016/0058625 A1* | 3/2016 | Morimoto | A61F 13/4942 604/385.27 |
| 2016/0206482 A1 | 7/2016 | Nishikawa et al. | |
| 2016/0206483 A1 | 7/2016 | Nishikawa et al. | |
| 2016/0206485 A1 | 7/2016 | Seitz et al. | |

FOREIGN PATENT DOCUMENTS

| | | |
|---|---|---|
| EP | 1827335 B1 | 6/2012 |
| EP | 2591758 A1 | 5/2013 |
| EP | 2601922 A1 | 6/2013 |
| EP | 1813239 B1 | 5/2014 |
| EP | 2813201 A1 | 12/2014 |
| FR | 2589047 A | 4/1987 |
| GB | 2283680 B | 11/1997 |
| JP | 01-119250 A | 5/1989 |
| JP | 01-272802 A | 10/1989 |
| JP | 02-010824 U1 | 1/1990 |
| JP | 02-291858 A | 12/1990 |
| JP | 03-121069 A | 5/1991 |
| JP | 03-123553 A | 5/1991 |
| JP | 04-067427 U1 | 6/1992 |
| JP | 3847679 B2 | 11/2006 |
| JP | 3847680 B2 | 11/2006 |
| JP | 4014471 B2 | 11/2007 |
| JP | 4180031 B2 | 11/2008 |
| JP | 4557905 B2 | 10/2010 |
| JP | 4557914 B2 | 10/2010 |
| JP | 4883924 B2 | 2/2012 |
| JP | 5578025 B2 | 8/2014 |
| JP | 5597449 B2 | 10/2014 |
| TW | 376315 B | 12/1999 |
| WO | WO 1986/001378 A1 | 3/1986 |
| WO | WO 1991/009582 A1 | 7/1991 |
| WO | WO 2012/117710 A1 | 9/2012 |
| WO | WO 2012/170778 A1 | 12/2012 |
| WO | WO 2012/170781 A1 | 12/2012 |
| WO | WO 2013/187376 A1 | 12/2013 |

* cited by examiner

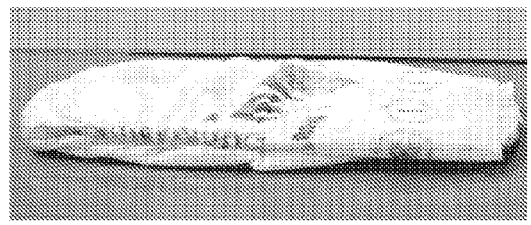
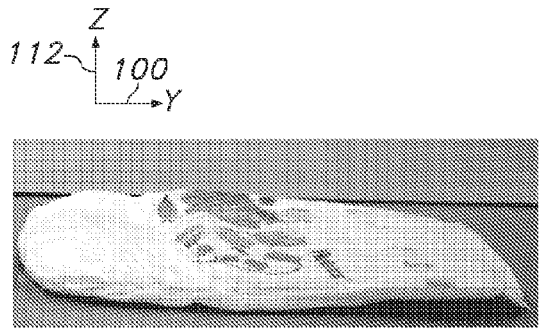
FIG. 7A-1
FIG. 7A-2
(PRIOR ART)
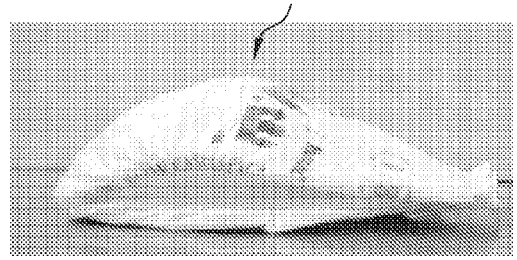
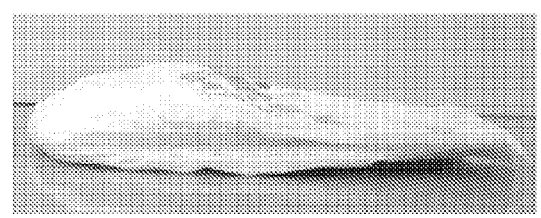
FIG. 7B-1
FIG. 7B-2
(PRIOR ART)
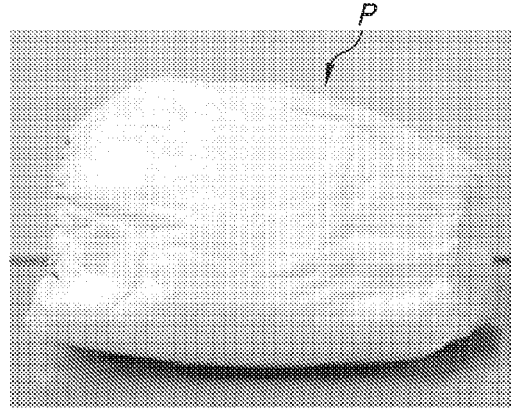
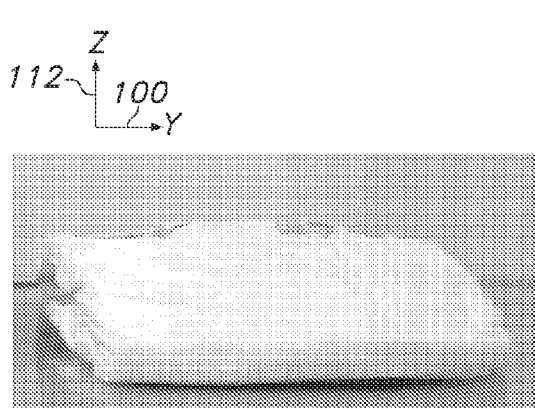
FIG. 7C-1
FIG. 7C-2
(PRIOR ART)

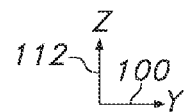
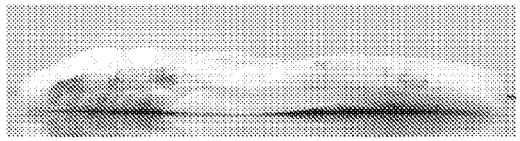 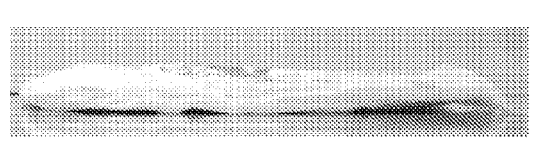
FIG. 9A-1  FIG. 9A-2 (PRIOR ART)
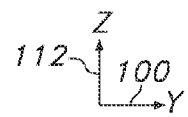
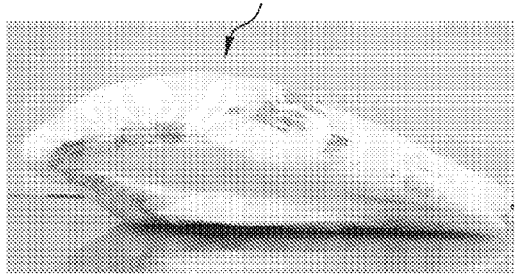 
FIG. 9B-1  FIG. 9B-2 (PRIOR ART)
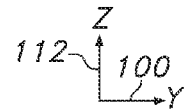
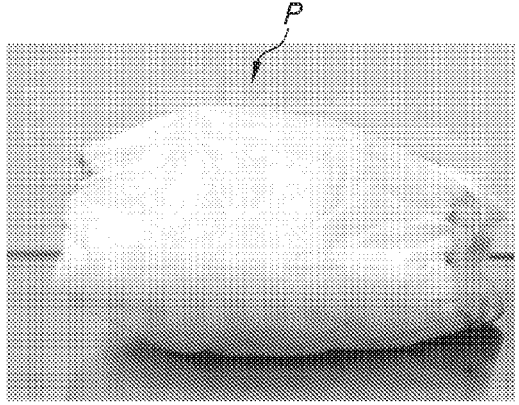 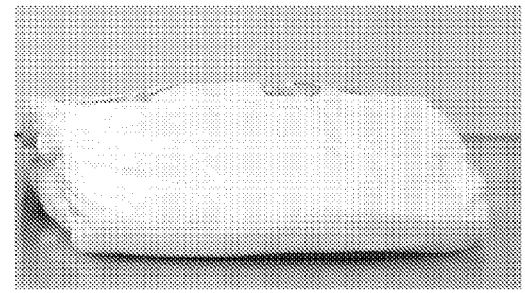
FIG. 9C-1  FIG. 9C-2 (PRIOR ART)

ABSORBENT ARTICLE WITH CHANNELS

TECHNICAL FIELD

The present disclosure relates to absorbent articles.

BACKGROUND OF THE DISCLOSURE

A primary function of personal care absorbent articles is to absorb and retain body exudates such as urine, fecal material, blood, and menses with additional desired attributes including low leakage of the exudates from the absorbent article and a dry feel to the wearer of the absorbent article. By preventing leakage of the exudates from the absorbent article, the absorbent article intends to prevent the body exudates from soiling or contaminating a wearer's or caregiver's clothing or other articles, such as bedding, that can come in contact with the wearer.

Another primary function of personal care absorbent articles is to provide a dry and comfortable feel not only prior to being soiled but afterwards as well. Many products are designed to keep the internal components of the product in direct contact with the body of the wearer, especially in the areas of insult by the wearer's body exudates and in particular urine. A decided disadvantage with this approach is that once the product has been soiled, the urine-wetted body side liner or topsheet remains in contact with the wearer's skin. The result is discomfort to the wearer due to constant contact with the wet surface. This contact with the skin can also lead to skin health problems which can require additional care or cause the product to be changed out more frequently to avoid the potential problem prior to full utilization of the capacity of the product. Yet another disadvantage is that the male and female anatomy is different and as a result, the area of insult on personal care absorbent articles is different for male genitalia versus female genitalia. As a result, if separation of the product from the wearer is to be achieved, the differences in anatomy must be taken into account.

Thus, there is a desire for improvements as to fit and comfort associated with absorbent articles to create structures which will take on predetermined shapes when opened and worn to reduce skin contact with the wearer thereby reducing the aforementioned disadvantages.

SUMMARY OF THE DISCLOSURE

The present invention is directed to personal care absorbent articles that employ a combination of void spaces, also referred to as channels, in the crotch region of the article in conjunction with shaping elastic members located outside the lateral side edges of the absorbent core, that, when coupled with strategic alignment of certain components and specifically-located folding lines, will create an article with improved convex or outward curvature of the chassis upon unfolding which provides increased spatial separation of the topsheet or body side liner of the article from the genital area of the wearer. In addition, due to the manipulation of the specific location of such elements in the article, gender specific product designs can be created which are specifically tailored to more appropriately deal with the differences in location of the male and female genitalia. As a result, an article is generated which provides better fit, less contact with insulted component materials of the article, better air circulation and an overall increased comfort and fit for the wearer.

In an embodiment, an absorbent article includes a chassis having a liquid-permeable topsheet, a liquid-impermeable backsheet and an absorbent core located between the topsheet and the backsheet. The chassis defines a longitudinal axis, a transverse axis and a z-directional axis orthogonal to the longitudinal and transverse axes. The chassis has a front waist region and a rear waist region separated by a crotch region. The chassis has opposed chassis end edges including a chassis front end edge and a chassis rear end edge and opposed chassis side edges. The absorbent article includes an absorbent core having opposed transverse absorbent core end edges, opposed longitudinal absorbent core side edges including a left side edge and a right side edge, and an absorbent core thickness. Optionally, the absorbent core can be wrapped by a core wrap on one or mode surfaces of the absorbent core. The absorbent core defines a plurality of channels therein extending through the absorbent core thickness with the channels being located in the crotch region and the front waist region of the chassis. The absorbent article has a pair of containment flaps each having a proximal end and a distal end with the proximal end of each of the pair of containment flaps being attached to the chassis in at least the crotch region and extending in the direction of the longitudinal axis. The proximal end of one of the pair of containment flaps is located outboard of the left side edge of the absorbent core and the proximal end of the other of the pair of containment flaps is located outboard of the right side edge of the absorbent core in the transverse direction. A pair of leg elastic members are attached to the chassis with one each of the pair of leg elastic members being positioned adjacent a respective chassis side edge in the crotch region of the article on opposite sides of the longitudinal axis. The absorbent article includes a pair of shaping elastic members extending in the direction of the longitudinal axis with one of the pair of shaping elastic members being located outboard of the left side edge of the absorbent core and the other of the pair of shaping elastic members being located outboard of the right side edge of the absorbent core. If an optional core wrap is being employed, the shaping elastics are located laterally outward and outside of the absorbent core wrap. Each of the pair of shaping elastic members is located in vertical juxtaposition with respect to the proximal end of a respective one of the pair of containment flaps relative to the direction of the z-directional axis in the crotch region of the absorbent article. The pair of shaping elastic members cause the chassis to have a convex shape in at least a portion of the front waist region or the crotch region.

In an embodiment, an absorbent article includes a chassis having a liquid-permeable topsheet, a liquid-impermeable backsheet and an absorbent core located between the topsheet and the backsheet. The chassis defines a longitudinal axis, a transverse axis and a z-directional axis orthogonal to the longitudinal and transverse axes. The chassis has a front waist region and a rear waist region separated by a crotch region. The chassis has opposed chassis end edges including a chassis front end edge and a chassis rear end edge and opposed chassis side edges. The absorbent article includes an absorbent core having opposed transverse absorbent core end edges, opposed longitudinal absorbent core side edges including a left side edge and a right side edge, and an absorbent core thickness. Optionally, the absorbent core can be wrapped by a core wrap on one or mode surfaces of the absorbent core. The absorbent core defines a plurality of channels therein extending through the absorbent core thickness with the channels being located in the crotch region and the front waist region of the chassis. The absorbent article has a pair of containment flaps each having a proximal end and a distal end with the proximal end of each of the pair of containment flaps being attached to the chassis in at least the crotch region and extending in the direction of the longitudinal axis. The proximal end of one of the pair of containment flaps is located outboard of the left side edge of the absorbent core and the proximal end of the other of the pair of containment flaps is located outboard of the right side edge of the absorbent core in the transverse direction. A pair of leg elastic members are attached to the chassis with one each of the pair of leg elastic members being positioned adjacent a respective chassis side edge in the crotch region of the article on opposite sides of the longitudinal axis. The absorbent article includes a pair of shaping elastic members extending in the direction of the longitudinal axis with one of the pair of shaping elastic members being located outboard of the left side edge of the absorbent core and the other of the pair of shaping elastic members being located outboard of the right side edge of the absorbent core. If an optional core wrap is being employed, the shaping elastics are located laterally outward and outside of the absorbent core wrap. Each of the pair of shaping elastic members is located in vertical juxtaposition with respect to the proximal end of a respective one of the pair of containment flaps relative to the direction of the z-directional axis in the crotch region of the absorbent article. The pair of shaping elastic members cause the chassis to have a convex shape in at least a portion of the front waist region or the crotch region. The article is folded prior to wearing along a first fold line on each side of the absorbent core outboard of a respective longitudinal absorbent core side edge of the absorbent core. Each the first fold line extends in the direction of the longitudinal axis with each of the first fold lines being in vertical juxtaposition relative to the Z-directional axis with one of the respective shaping elastic members and the proximal ends of the containment flaps in the crotch region. The folding causes the respective leg elastic members to be folded inwardly over a body-facing side of the absorbent core.

In an embodiment, the absorbent article can be further folded in the crotch region prior to wearing along a transverse second fold line in the direction of the transverse axis.

In an embodiment, the transverse second fold line in the absorbent article extends through the channels and shaping elastic members.

In an embodiment, the backsheet of the absorbent article has a body facing layer and a garment facing layer with the shaping elastic members being located between the body facing layer and the garment facing layer of the backsheet.

In an embodiment, the shaping elastic members of the absorbent article are located predominantly in the crotch region and the front waist region of the chassis.

In an embodiment, the shaping elastic members of the absorbent article are located predominantly in the crotch region and the rear waist region of the chassis.

In an embodiment, the shaping elastics of the absorbent article can be located predominately in the crotch region of the chassis.

In an embodiment, the plurality of channels in the absorbent article are positioned more towards the front waist region and the chassis front end edge than the rear waist region.

In an embodiment, the channels in the absorbent article are each defined by a front end and a rear end, and the shaping elastic members each have a front end and a rear end. The front end and the rear end of the shaping elastic members are respectively forward of the front end and the rear end of the channels and therefore closer to the chassis front end edge than are the front end and the rear end of the channels.

In an embodiment, the channels of the absorbent article each define a front end and a rear end, and the shaping elastics each have a front end and a rear end. The front end and the rear end of the shaping elastic members are respectively rearward of the front end and the rear end of the channels and therefore closer to the chassis rear end edge than are the front end and the rear end of the channels.

In an embodiment, the channels in the absorbent article are each defined by a front end and a rear end, and the shaping elastic members each have a front end and a rear end. The front end and the rear end of the shaping elastic members are respectively rearward of the front end and the rear end of the channels and therefore closer to the chassis rear end edge than are the front end and the rear end of the channels.

In an embodiment, the shaping elastics in the absorbent article have a length and the channels in the absorbent core define a length. The length of the shaping elastic members is generally equal to the length of the channels in the absorbent core.

In an embodiment, the shaping elastics in the absorbent article have a length and the channels in the absorbent core define a length. The length of the shaping elastics is longer than the length of the channels in the absorbent core.

A method of creating and folding an absorbent article is also disclosed. The method involves first creating an absorbent article by positioning an absorbent core between a liquid pervious topsheet and a liquid impervious backsheet to form a chassis. The chassis defines a longitudinal axis, a transverse axis and a z-directional axis orthogonal to the longitudinal and transverse axes. The chassis has a front waist region and a rear waist region separated by a crotch region. The chassis has opposed chassis end edges including a chassis front end edge and a chassis rear end edge and opposed chassis side edges. The absorbent core has opposed transverse absorbent core end edges, opposed longitudinal absorbent core side edges including a left side edge and a right side edge, and an absorbent core thickness.

A plurality of channels are created in the absorbent core extending through the absorbent core thickness with the channels being located in the crotch region and the front waist region of the chassis.

A pair of containment flaps are attached to the chassis with each of the pair of containment flaps having a proximal end and a distal end. The proximal end of each of the pair of containment flaps is attached to the chassis in at least the crotch region and extends in the direction of the longitudinal axis. The proximal end of one of the pair of containment flaps is located outboard of the left side edge of the absorbent core and the proximal end of the other of the pair of containment flaps is located outboard of the right side edge of the absorbent core.

A pair of leg elastic members are attached to the chassis with one of the pair of the leg elastic members being located on either side of the longitudinal axis adjacent a respective chassis side edge.

A pair of shaping elastic members are attached to the chassis extending in the direction of the longitudinal axis with one of the pair of shaping elastic members being located outboard of the left side edge of the absorbent core and the other of the pair of shaping elastic members being located outboard of the right side edge of the absorbent core.

Each one of the pair of shaping elastic members is located in vertical juxtaposition with respect to the proximal end of a respective one of the pair of containment flaps relative to the direction of the z-directional axis in the crotch region.

One the absorbent article is formed, it is folded along a first fold line on each side of the absorbent core outboard of a respective longitudinal absorbent core side edge of the absorbent core. Each of the first fold lines extends in the direction of the longitudinal axis with each the first fold lines being in vertical juxtaposition relative to the Z-directional axis with one of the respective shaping elastic members and the proximal end of one of the containment flaps. Thus, there are a pair of folding lines. The folding causes the respective leg elastic members on either side of the product to be folded inwardly over a body-facing side of the absorbent core. Finally, the absorbent article is folded in the crotch region along a transverse second fold line in the direction of the transverse axis such that the front waist edge and the rear waist edge are generally aligned with one another.

In an embodiment, the method of folding can cause the transverse second fold line to extend through the channels and shaping elastic members.

In an embodiment, the method forming step can cause the plurality of channels to be created more towards the from waist region than the rear waist region and therefore closer to the chassis front end edge than the chassis rear end edge.

In an embodiment of the method the backsheet of the absorbent article can have a body facing layer and garment facing layer such that the shaping elastic members can be located between the body facing layer and the garment facing layer of the absorbent article.

BRIEF DESCRIPTION OF DRAWINGS

A full and enabling disclosure thereof, directed to one of ordinary skill in the art, is set forth more particularly in the remainder of the specification, which makes reference to the appended figures in which:

FIG. 7A-1 is a photograph of a side perspective view of a male version of an absorbent article, having a construction as is shown in FIG. 1A, when in a folded state as it would look when first removed from a package of compressed absorbent articles according to the present invention.

FIG. 7A-2 is a photograph of a side perspective view of a prior art conventional absorbent article in a folded state as it would look when first removed from a package of compressed absorbent articles.

FIG. 7B-1 is a photograph of a side perspective view of a male version of an absorbent article, having a construction as is shown in FIG. 1A, when in a folded state as it would look after it had been removed from a package of compressed absorbent articles, opened fully and then refolded showing the enhanced curvature of the absorbent article according to the present invention.

FIG. 7B-2 is a photograph of a side perspective view of a prior art conventional absorbent article in a folded state as it would look after it had been removed from a package of compressed absorbent articles, opened fully and then refolded.

FIG. 7C-1 is a photograph of an end perspective view of a male version of an absorbent article, having a construction as is shown in FIG. 1A, when in a folded state as it would look after it had been removed from a package of compressed absorbent articles, opened fully and then refolded showing the enhanced curvature of the absorbent article according to the present invention.

FIG. 7C-2 is a photograph of an end perspective view of a prior art conventional absorbent article in a folded state as it would look after it had been removed from a package of compressed absorbent articles, opened fully and then refolded.

FIG. 8A-1 is a photograph of a side perspective view of a female version of an absorbent article, having a construction as is shown in FIG. 1B, when in a folded state as it would look when first removed from a package of compressed absorbent articles according to the present invention.

FIG. 8A-2 is a photograph of a side perspective view of a prior art conventional absorbent article in a folded state as it would look when first removed from a package of compressed absorbent articles.

FIG. 8B-1 is a photograph of a side perspective view of a female version of an absorbent article, having a construction as is shown in FIG. 1B, when in a folded state as it would look after it had been removed from a package of compressed absorbent articles, opened fully and then refolded showing the enhanced curvature of the absorbent article according to the present invention.

FIG. 8B-2 is a photograph of a side perspective view of a prior art conventional absorbent article in a folded state as it would look after it had been removed from a package of compressed absorbent articles, opened fully and then refolded.

FIG. 8C-1 is a photograph of an end perspective view of a female version of an absorbent article, having a construction as is shown in FIG. 1B, when in a folded state as it would look after it had been removed from a package of compressed absorbent articles, opened fully and then refolded showing the enhanced curvature of the absorbent article according to the present invention.

FIG. 8C-2 is a photograph of an end perspective view of a prior art conventional absorbent article in a folded state as it would look after it had been removed from a package of compressed absorbent articles, opened fully and then refolded.

FIG. 9A-1 is a photograph of a side perspective view of a unisex version of an absorbent article, having a construction as is shown in FIG. 1C, when in a folded state as it would look when first removed from a package of compressed absorbent articles according to the present invention.

FIG. 9A-2 is a photograph of a side perspective view of a prior art conventional absorbent article in a folded state as it would look when first removed from a package of compressed absorbent articles.

FIG. 9B-1 is a photograph of a side perspective view of a unisex version of an absorbent article, having a construction as is shown in FIG. 1C, when in a folded state as it would look after it had been removed from a package of compressed absorbent articles, opened fully and then refolded showing the enhanced curvature of the absorbent article according to the present invention.

FIG. 9B-2 is a photograph of a side perspective view of a prior art conventional absorbent article in a folded state as it would look after it had been removed from a package of compressed absorbent articles, opened fully and then refolded.

FIG. 9C-1 is a photograph of an end perspective view of a unisex version of an absorbent article, having a construction as is shown in FIG. 1C, when in a folded state as it would look after it had been removed from a package of compressed absorbent articles, opened fully and then refolded showing the enhanced curvature of the absorbent article according to the present invention.

FIG. 9C-2 is a photograph of an end perspective view of a prior art conventional absorbent article in a folded state as it would look after it had been removed from a package of compressed absorbent articles, opened fully and then refolded.

Figure 1A:
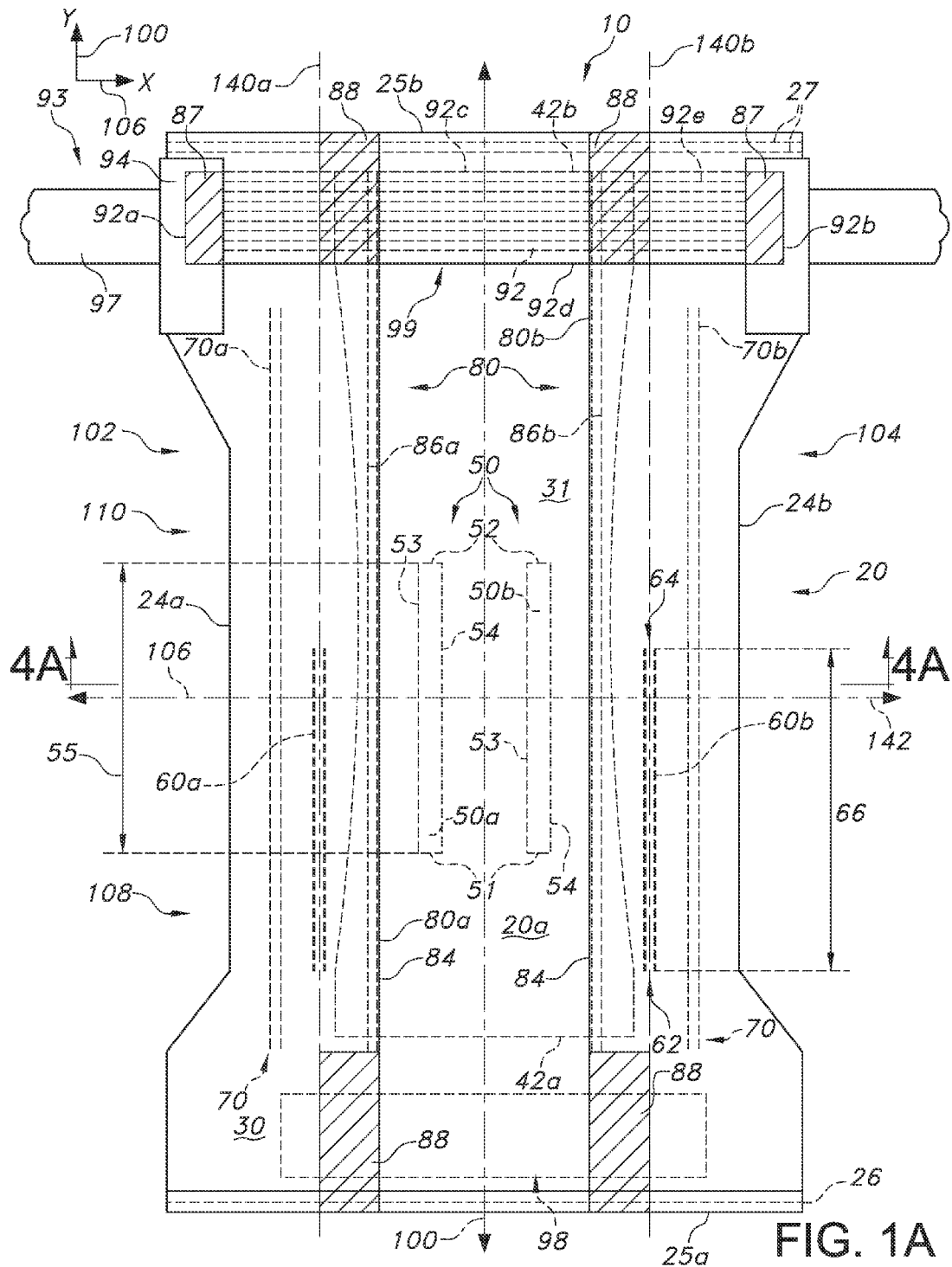
FIG. 1A is top plan view of an exemplary embodiment of a male version of an absorbent article, such as a diaper, in a stretched out and laid flat configuration according to the present invention.
Figure 1B:
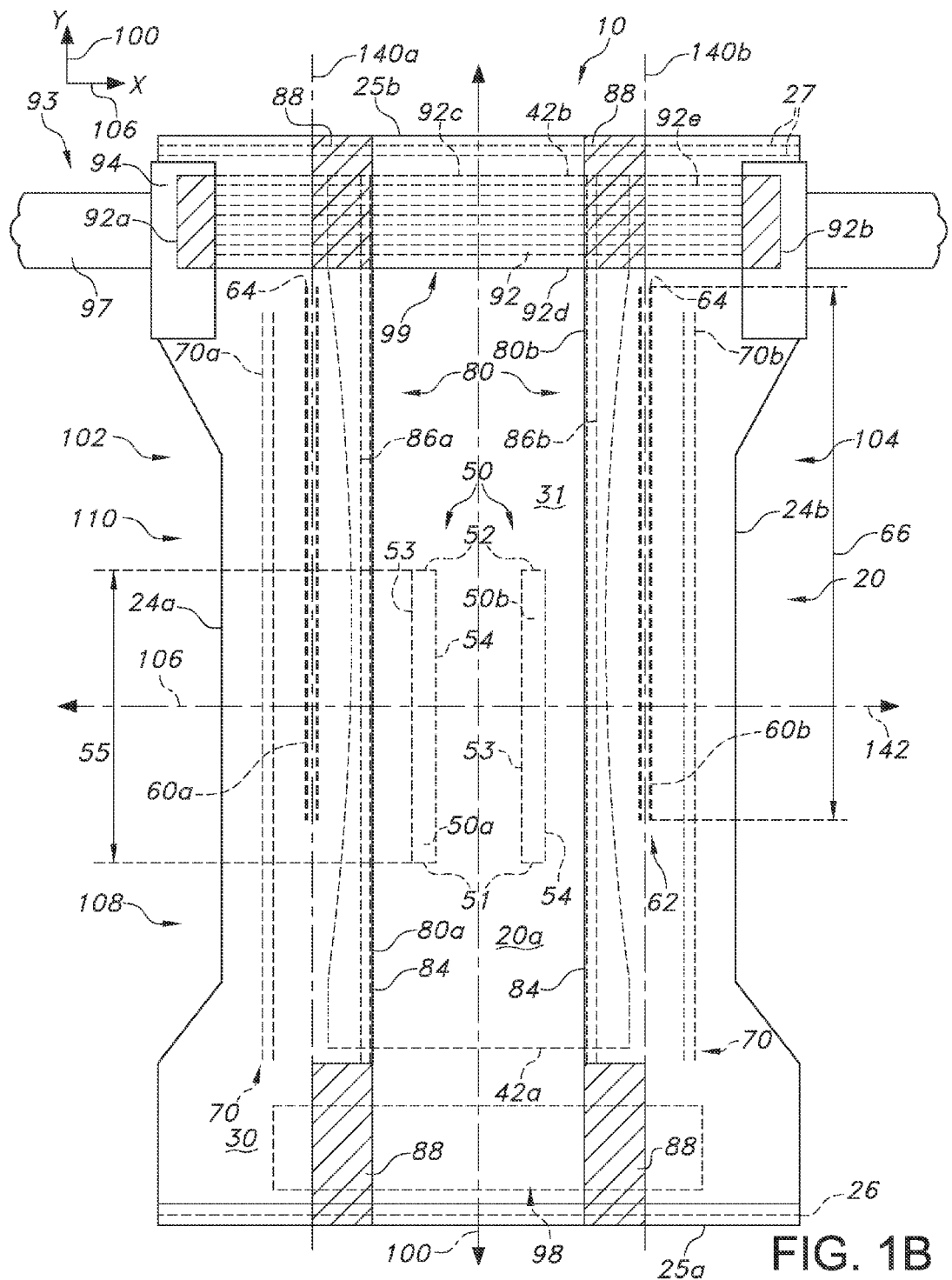
FIG. 1B is top plan view of an exemplary embodiment of a female version of an absorbent article, such as a diaper, in a stretched out and laid flat configuration according to the present invention.
Figure 1C:
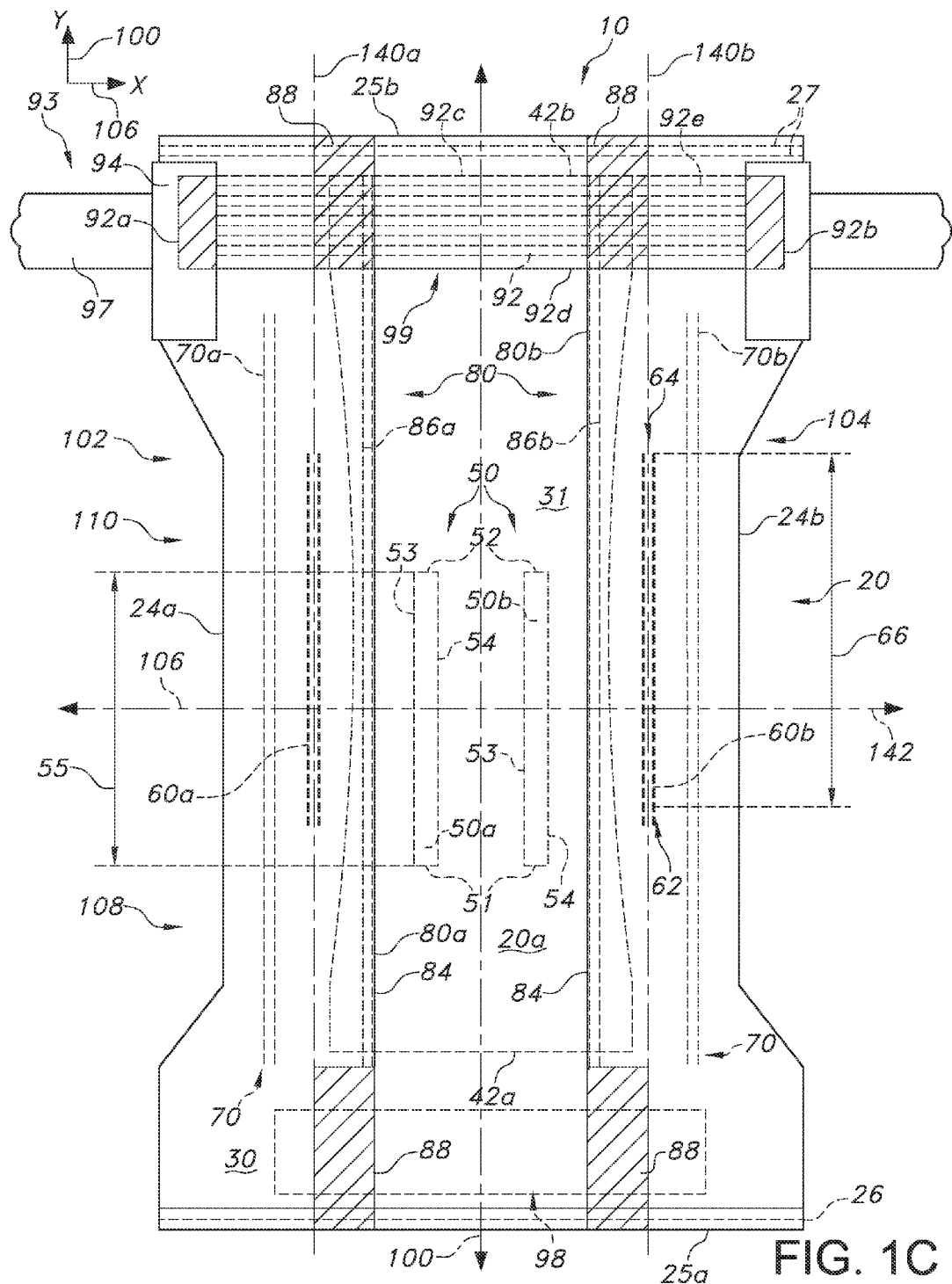
FIG. 1C is top plan view of an exemplary embodiment of a unisex version of an absorbent article, such as a diaper, in a stretched out and laid flat configuration according to the present invention.
Figures 1, 2, 8A:
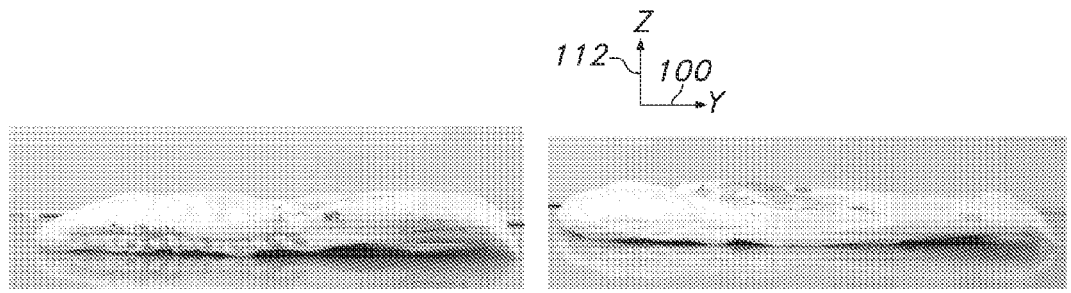

Note that when, for example, the reader is directed to "FIG. 1", that this includes FIGS. 1A, 1B and 1C unless specifically noted. The same is true for the other Figure numbers which have multiple sub-numbered drawings.

DETAILED DESCRIPTION OF THE DISCLOSURE

In an embodiment, the present disclosure is generally directed towards an absorbent article having a waist containment member. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

Figure 10:
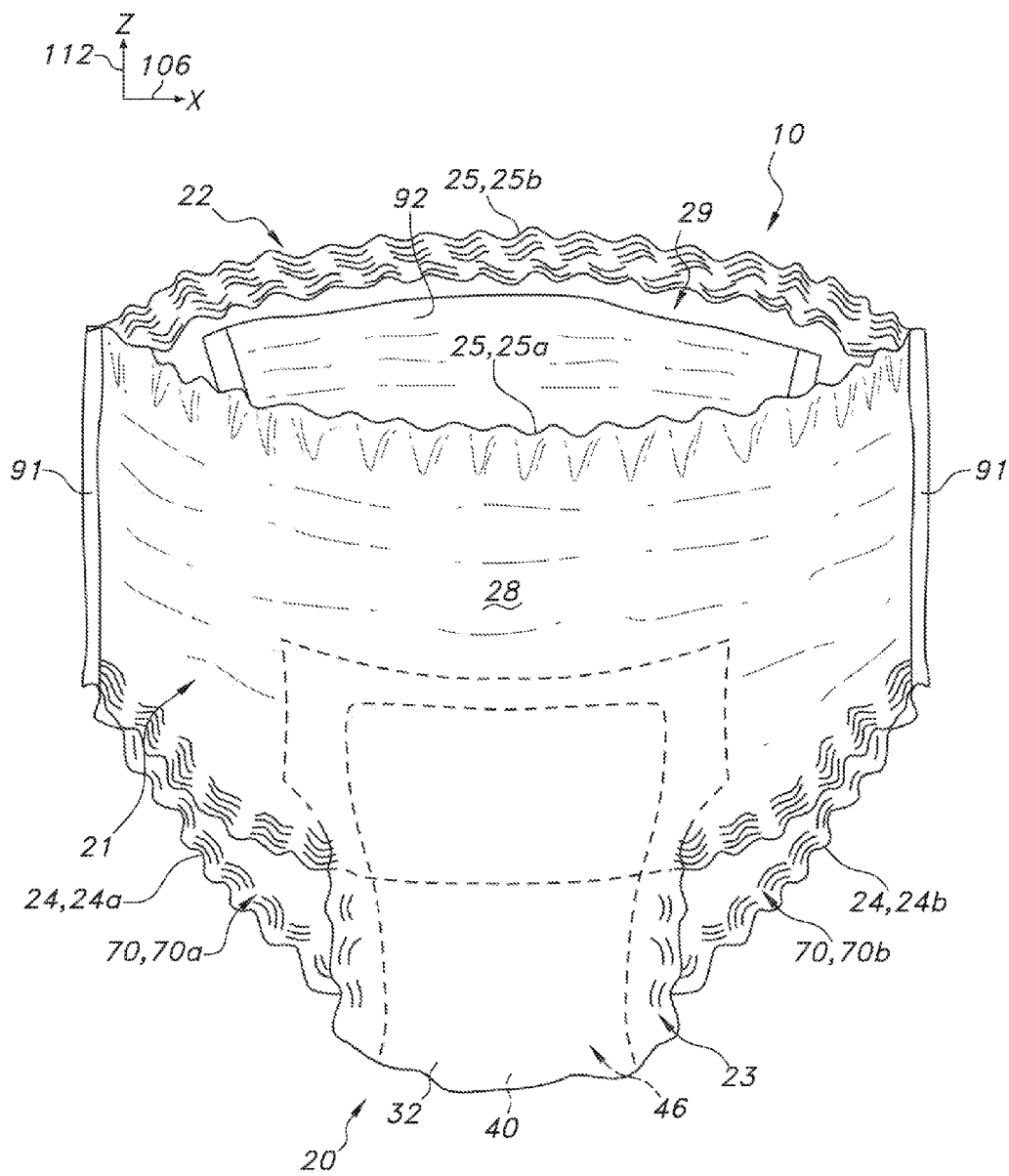
FIG. 10 is a perspective view of an exemplary embodiment of male version of an absorbent article, such as a training pant according to the present invention.

Absorbent Article:

Referring to the Figures as a whole and in particular to FIGS. 1-6, a non-limiting illustration of an absorbent article 10 for example, a diaper, is illustrated. Other embodiments of the absorbent article could include, but are not limited to, training pants, youth pants, adult incontinence garments, and feminine hygiene articles. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the transverse direction of the product, which hereinafter is called the cross direction manufacturing of a product, without departing from the spirit and scope of the disclosure. For example, the absorbent article 10 in FIG. 10 provides an exemplary embodiment of an absorbent article 10 that can be manufactured in cross-direction manufacturing process.

The absorbent article 10 as shown in the Figures has a longitudinal axis and direction 100 which bisects the absorbent article 10 into a left side region 102 and a right side region 104. The absorbent article 10 as shown in the Figures has a lateral or transverse axis and direction 106 which bisects the absorbent article 10 into a front half or region 108 and a rear half or region 110. The absorbent article 10 as shown in the Figures also has a vertical or Z-directional axis 112 which is orthogonal to the longitudinal and transverse axes 100 and 106. See FIGS. 4A and 4B.

The absorbent article 10 illustrated in FIGS. 1-6 and 10 and 11 each include a chassis 20. The absorbent article 10 can include a front waist region 21, a rear waist region 22, and a crotch region 23 disposed between the front waist region 21 and the rear waist region 22 and interconnecting the front and rear waist regions, 21, 22, respectively. See FIG. 3 The front waist region 21 can be referred to as the front end region, the rear waist region 22 can be referred to as the rear end region, and the crotch region 23 can be referred to as the intermediate region. In the embodiment depicted in FIGS. 10 and 11, a three-piece construction of an absorbent article 10 is depicted where the absorbent article 10 can have a chassis 20 including a front waist panel 28 defining the front waist region 21, a rear waist panel 29 defining the rear waist region 22, and an absorbent panel 46 defining the crotch region 23 of the absorbent article 10. The absorbent panel 46 can extend between the front waist panel 28 and the rear waist panel 29. In some embodiments, the absorbent panel 46 can overlap the front waist panel 28 and the rear waist panel 29. The absorbent panel 46 can be bonded to the front waist panel 28 and the rear waist panel 29 to define a three-piece construction. However, it is contemplated that an absorbent article can be manufactured in a cross-direction without being a three-piece construction garment which is also sometimes referred to as a one-piece construction (not shown) as the front waist panel 28 and the rear waist panel 29 are integral with one another by way of commonly connected components forming the waist panels such as a liquid permeable topsheet and/or a liquid impermeable backsheet which can envelope the absorbent panel 46.

The absorbent article 10 and the chassis in particular has opposed chassis longitudinal side edges 24 and opposed chassis transverse side edges 25. There is shown a pair of longitudinal side edges 24, respectively designated left side edge 24a and right side edge 24b, and a pair of opposite transverse waist end edges 25 respectively designated front waist edge 25a and rear waist edge 25b. The front waist region 21 can be contiguous with the front waist edge 25a and the rear waist region 22 can be contiguous with the rear waist edge 25b. The longitudinal side edges 24a and 24b can extend from the front waist edge 25a to the rear waist edge 25b. The longitudinal side edges 24a and 24b can extend in a direction parallel to the longitudinal axis 100 for their entire length, such as for the absorbent articles 10 illustrated in FIGS. 1 and 2. In other embodiments (not shown), the longitudinal side edges 24a, 24b can be curved between the front waist edge 25a and the rear waist edge 25b. In the absorbent article 10 of FIG. 11, the longitudinal side edges 24a, 24b can include portions of the front waist panel 28, the absorbent panel 46, and the rear waist panel 29.

The front waist region 21 can include the portion of the absorbent article 10 that, when worn, is positioned at least in part on the front of the wearer while the rear waist region 22 can include the portion of the absorbent article 10 that, when worn, is positioned at least in part on the back of the wearer. The crotch region 23 of the absorbent article 10 can include the portion of the absorbent article 10 that, when worn, is positioned between the legs of the wearer and can partially cover the lower torso of the wearer. The waist edges, 25a and 25b, of the absorbent article 10 are configured to encircle the waist of the wearer and together define a central waist opening for the waist of the wearer. Portions of the longitudinal side edges 24a, 24b in the crotch region 23 can generally define leg openings for the legs of the wearer when the absorbent article 10 is worn. See FIG. 4A.

Figure 4B:
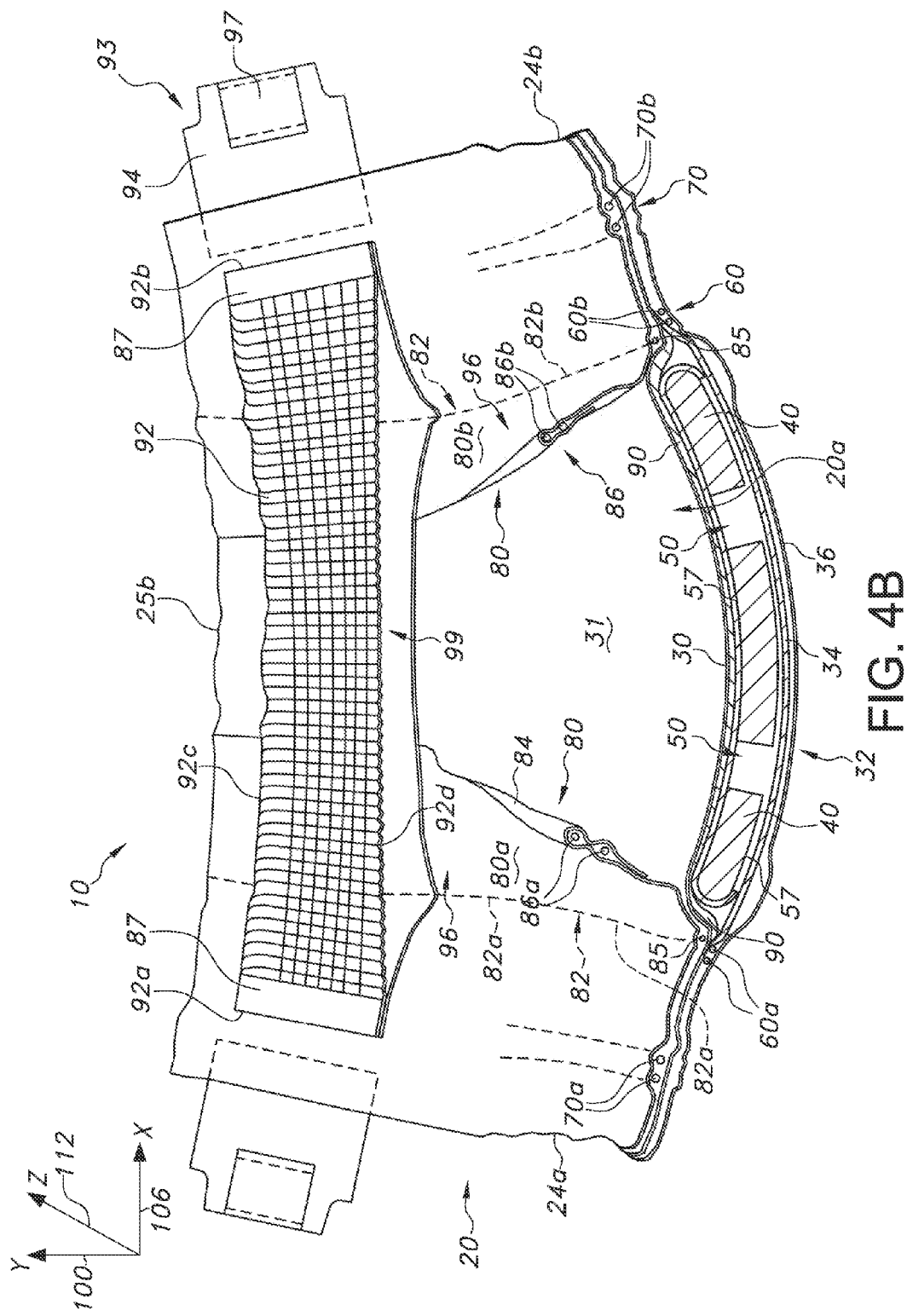
FIG. 4B is a frontal cross-sectional perspective view of the absorbent article of FIG. 1A taken along line 4-4 in FIG. 1A with the absorbent article being in a relaxed configuration.
Figure 5:
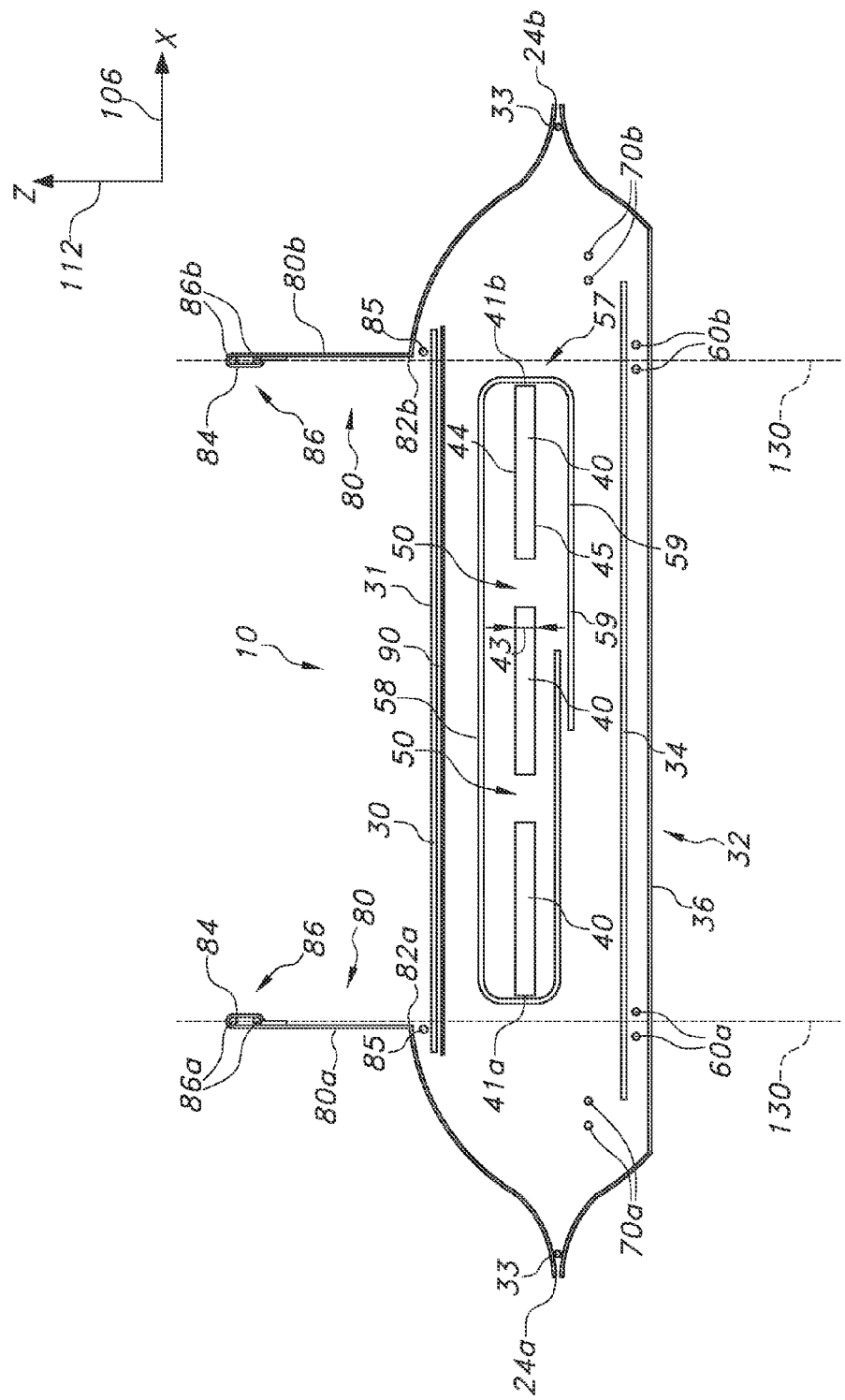
FIG. 5 is a schematic cross-sectional end view of the absorbent article of FIG. 1A along line 4-4 of FIG. 1A.

The absorbent article 10 can include a liquid permeable topsheet 30 and a liquid impermeable backsheet 32. The topsheet 30 and the backsheet 32 can form a portion of the chassis 20. In an embodiment, the topsheet 30 can be bonded to the backsheet 32 in a superposed relation by any suitable means 33 such as, but not limited to, adhesives, ultrasonic bonds, thermal bonds, pressure bonds, or other conventional techniques. The topsheet 30 and the backsheet 32 can each define a length in a longitudinal direction 100, and a width in the transverse direction 106, which, in the illustrated embodiment, can coincide with the length and width of the absorbent article 10. Both the topsheet 30 and the backsheet 32 can each be formed from a single layer of material or multiple layers of material. As represented in FIGS. 4B and 5, the backsheet 32 includes a body facing layer 34 and a garment facing layer 36.

The chassis 20 can include an absorbent core 40. The absorbent core 40 can be disposed between the topsheet 30 and the backsheet 32. The absorbent core 40 can have longitudinal side edges 41, respectively left longitudinal side edge 41a and right longitudinal side edge 41b, which, in an embodiment, can form portions of the longitudinal side edges 24a and 24b, respectively, of the absorbent article 10. The absorbent core 40 can have absorbent core transverse end edges 42 including a front end edge 42a that is opposite a rear end edge 42b, respectively, which, in an embodiment, can form portions of the waist edges, 25a and 25b, respectively, of the absorbent article 10. The absorbent core 40 has an absorbent core body facing side or surface 44 and an absorbent core garment facing side or surface 45 which define an absorbent core thickness 43 therebetween. In an embodiment, the absorbent core 40 can have a length and width that are the same as or less than the length and width of the absorbent article 10.

The absorbent core 40 typically is composed of wood pulp fluff and a highly absorbent material commonly referred to as a hydrogel or superabsorbent material which will retain many times its own weight in body exudates such as urine. Due to the rigors of wear and use, it is not uncommon for such materials to break loose and move to other locations within the absorbent article 10. As a result, if desired, the absorbent core 40 can be enveloped by what is termed a core wrap 57 which is used to contain the wood pulp and superabsorbent. As shown in cross-section in FIGS. 4B and 5, the core wrap 57 will wrap the upper or body facing surface 44 and the lower or garment facing surface 45 of the absorbent core 40 and thus will have a core wrap upper layer 58 and a core wrap lower layer 59. The upper and lower layers 58 and 59 may be the same material or different materials if so desired. Typical materials used for the core wrap include tissue and fibrous nonwoven webs such as meltblown, spunbond or combinations of meltblown and spunbond. To further improve the integrity of the absorbent core 40, the core wrap 57 may be adhered to the absorbent core 40 through the use of adhesives or other means known to those of ordinary skill in the art.

Figure 11:
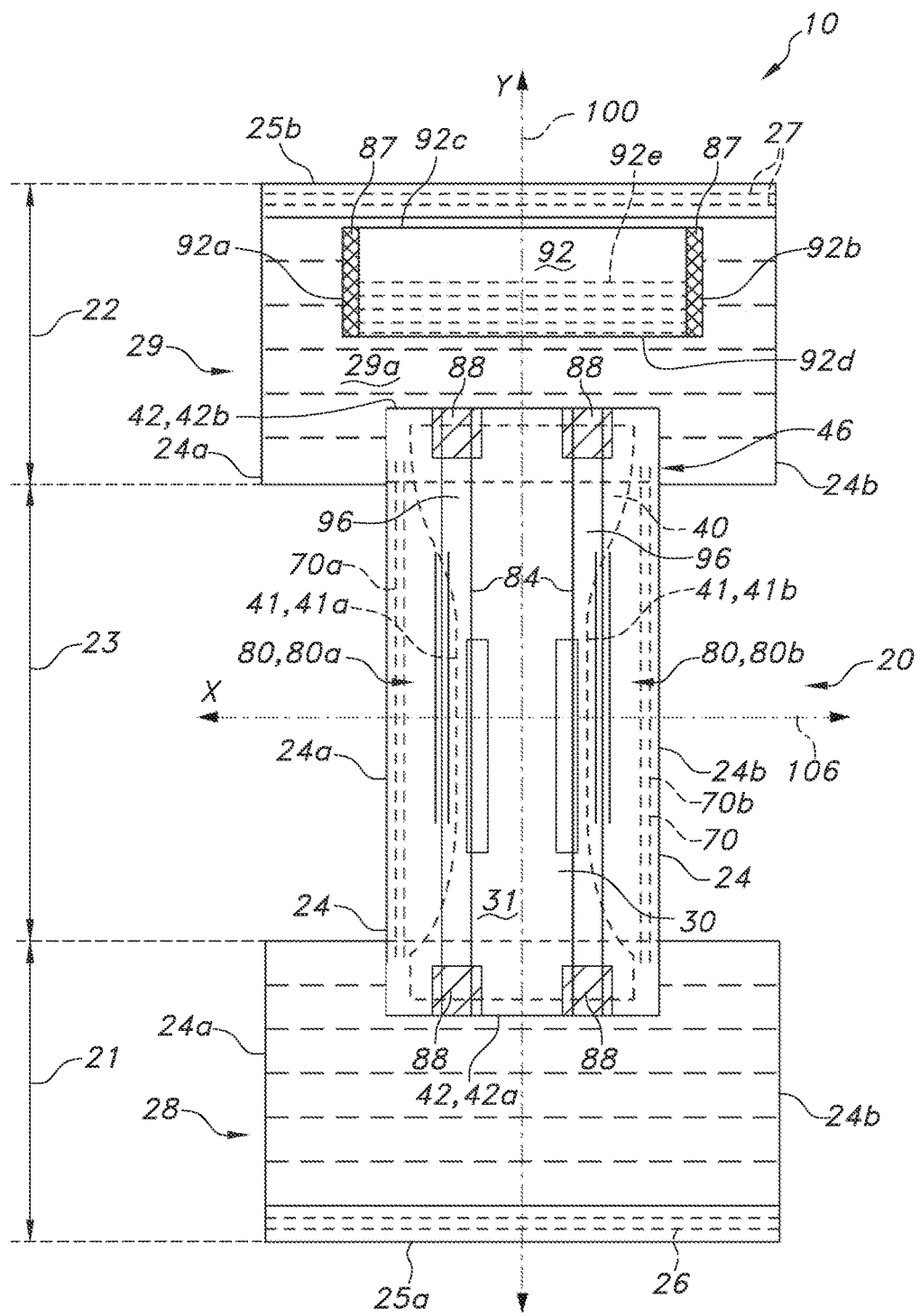
FIG. 11 is top plan view of an exemplary embodiment of a unisex version of an absorbent article, such as a training pant, in a stretched out and laid flat configuration according to the present invention.

Referring to FIGS. 10 and 11, the topsheet 30, backsheet 32, and the absorbent core 40 can collectively form all or part of an absorbent panel 46. This is particularly desirable when the absorbent panel is the only structure spanning the front waist panel 28 and the rear waist panel 29.

In addition to the topsheet 30, backsheet 32 and absorbent core 40, the absorbent article 10 can include an optional acquisition layer 90 located between the topsheet 30 and the absorbent core 40. The purpose of the acquisition layer 90 is to quickly take up body exudates delivered to it from the topsheet 30, temporarily hold such exudates and then transfer them to the underlying absorbent core 40. Such acquisition layers can be made from fibrous nonwoven webs including, but not limited to, spunbond webs, meltblown webs and staple fiber webs such as through air bonded carded webs and hydroentangled webs as well as combinations of the foregoing and still further, apertured films.

The absorbent article 10 can be configured to contain and/or absorb liquid, solid, and semi-solid body exudates discharged from the wearer. In some embodiments, containment flaps 80 can be configured to provide a barrier to the lateral flow of body exudates. The containment flaps 80 include a left containment flap 80a and a right containment flap 80b. To further enhance containment and/or absorption of body exudates, the absorbent article 10 can optionally include a waist containment member 92 which forms a pocket 99 with the chassis 20. In some embodiments, the waist containment member 92 can be disposed in the rear waist region 22 of the absorbent article 10. Although not depicted herein, it is contemplated that the waist containment member 92 can be additionally or alternatively disposed in the front waist region 21 of the absorbent article 10.

The waist containment member 92 can be disposed on the body facing surface 20a of the chassis 20 to help contain and/or absorb body exudates. In some embodiments, such as in the absorbent article 10 depicted in FIGS. 1, 2, 4B, 6 and 11, the waist containment member 92 can be disposed on the body facing surface 31 of the topsheet 30. In some embodiments, such as in the absorbent article 10 depicted in FIG. 11, the waist containment member 92 can be disposed on the body facing surface 29a of the rear waist panel 29.

Figure 2:
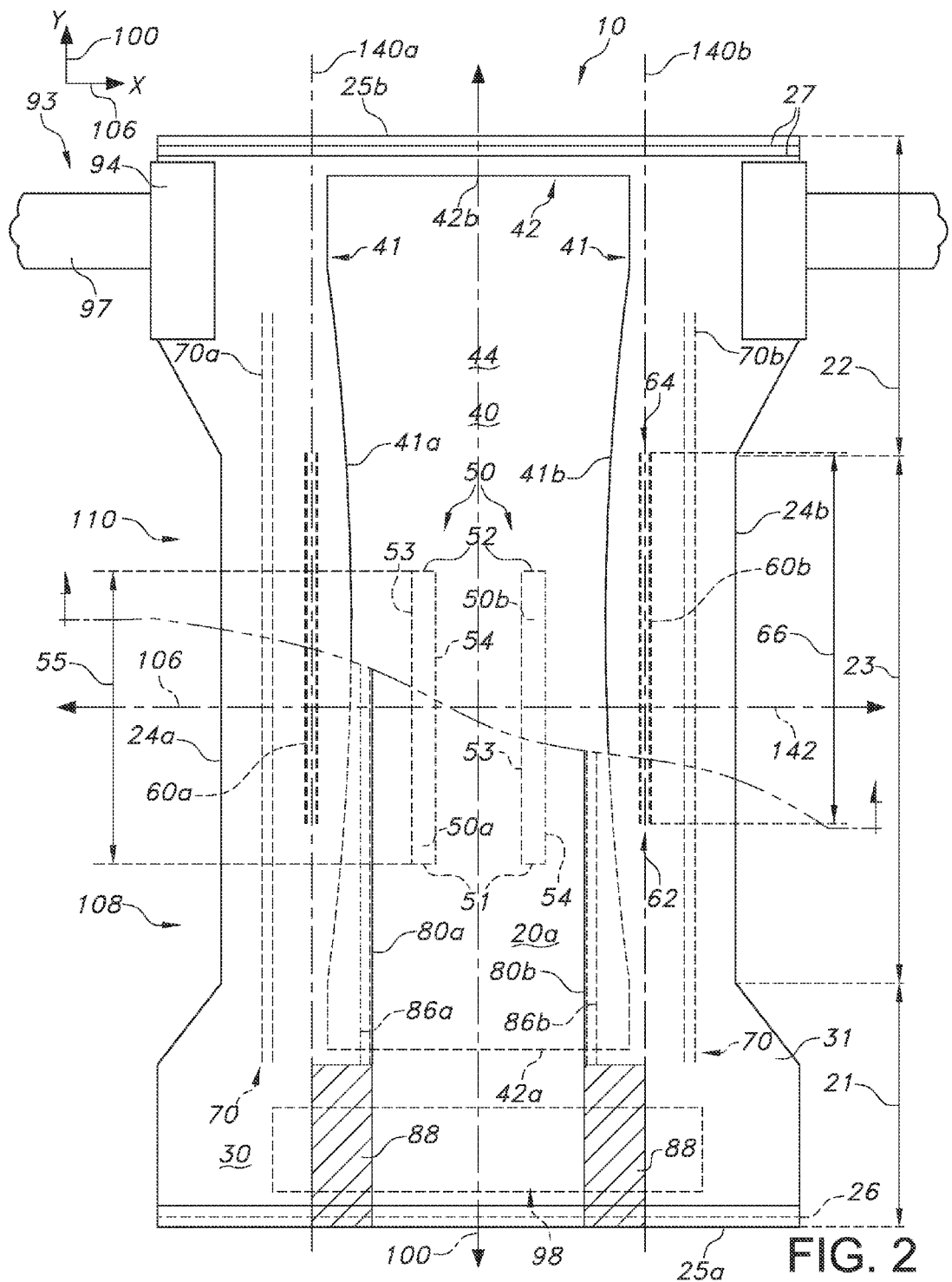
FIG. 2 is a partial cut-away top plan view of the absorbent article of FIG. 1C.

The absorbent article 10 can further include leg elastic members 70 as are known to those of ordinary skill in the art. The leg elastic members 70 can be attached to the backsheet 32 and/or the topsheet 30 along the opposite longitudinal side edges, 24a and 24b, and positioned in the crotch region 23 of the absorbent article 10 so as to form a left side leg elastic member 70a and a right side leg elastic member 70b. The leg elastic members 70 can be parallel to the longitudinal axis 100 as shown in FIGS. 1, 2 and 11 or can be curved as is known in the art. The leg elastic members 70 in conjunction with the other materials to which they are attached can provide elasticized leg cuffs.

When the absorbent article 10 being worn is an open diaper such as is shown in FIGS. 1-6, a fastening system 93 is used to secure the product about the torso of the wearer. As shown in FIGS. 1, 2 and 4A, the fastening system 93 in the rear waist region 22 includes a pair of ear flaps 94, all or a portion of which may be inelastic, stretchable or elastic and a fastener 97 such as a mechanical hook or loop or an adhesive tape. The ear flaps 94 can be separate and attached to the chassis 20 or they can be integral with the chassis 20 and formed from one or more of the other components such as the topsheet 30 and/or the backsheet 32. A complementary portion of the fastening system 93 is located in the front waist region 21 of the absorbent article 10. As shown in FIGS. 1, 2 and 4A, a landing zone material 98 in located on the garment facing side of the absorbent article 10 midway between the lateral side edges 24a and 24b. If the fastener 97 in the rear waist region 22 is a hook material, then the landing zone material 98 in the front waist region 21 can comprise a loop material which will engage with the hooks of the fastener 97. Alternatively, the location of the hook and loop materials may be reversed. Still further, if the fastener 97 is an adhesive tape, then the landing zone member 98 can be a relatively smooth-surfaced material such as a plastic film which will readily adhere to the adhesive tape of the fastener 97. In many situations where the garment facing side of the backsheet 32 is a plastic film, the backsheet 32 can also serve the purpose of the landing zone material 98.

When the absorbent article 10 being worn is a closed article such as a training pant as is shown in FIGS. 10 and 11, the lateral side edges of the front 28 and rear 29 waist panels will be joined to one another in either a fixed or refastenable configuration. In a fixed configuration, the side seams 91 can be formed adhesively or through the use of thermal bonding as with the use of heat and pressure or ultrasonics. In a refastenable configuration, the side seams may include strips of hook and loop fastening material (not shown) to form the side seams 91 so the product can be taken on an off so as to check for soiling.

To further retain the absorbent article about the torso of the wearer, the front waist region 21 and the rear waist region 22 of the articles 10 in FIGS. 1, 2, 10 and 11 may be fitted with additional waist elastic elements adjacent the open waist of the respective product. The front waist region 21 may include front waist elastics 26 and the rear waist region 22 may include rear waist elastics 27. The elastics 26 and 27 may be located on an exterior surface of the article 10 such as the body facing surface and/or the garment facing surface or they may be located internally as between the topsheet 30 and the backsheet 32. The elastic elements 26, 27 may be made from the same or different materials as are used to form the other elastic elements of the absorbent article 10 described herein including, but limited to, the leg elastic members 70. Exemplary elastic materials include, elastic strands and ribbons, elastic films and combinations of the foregoing in combination with other materials such as fibrous nonwoven webs to form elastic laminates.

Additional details regarding these elements of the absorbent article 10 described herein can be found below and with reference to the FIGS. 1-11:

Topsheet or Bodyside Liner:

The topsheet 30 of the absorbent article 10 can overlay the absorbent core 40 and the backsheet 32 and can isolate the wearer's skin from liquid waste retained by the absorbent core 40. In various embodiments, an acquisition layer 90 can be positioned between the topsheet 30 and the absorbent core 40. In various embodiments, the topsheet 30 can be bonded to the transfer layer 90 via adhesive and/or by a point fusion bonding. The point fusion bonding may be selected from ultrasonic, thermal, pressure bonding, and combinations thereof.

In an embodiment, the topsheet 30 can extend beyond the absorbent core 40 and/or an acquisition layer 90, if present, to overlay a portion of the backsheet 32 and can be bonded thereto by any method deemed suitable, such as, for example, by being bonded thereto by adhesive 33, to substantially enclose the absorbent core 40 between the backsheet 32 and the topsheet 30. It is contemplated that the topsheet 30 may be narrower than the backsheet 32. However, in other embodiments, the topsheet 30 and the backsheet 32 may be of the same dimensions in width and length, for example, as depicted in the embodiments illustrated in FIGS. 1-4. In other embodiments, the topsheet 30 can be of greater width than the backsheet 32. It is also contemplated that the topsheet 30 may not extend beyond the absorbent core 40 and/or may not be secured to the backsheet 32 and/or may be secured to the backsheet 32 through an intermediate layer such as the acquisition layer 90. In some embodiments, the topsheet 30 can wrap at least a portion of the absorbent core 40, including wrapping around both longitudinal edges 41a and 41b of the absorbent core 40, and/or one or more of the end edges 42a and 42b. It is further contemplated that the topsheet 30 may be composed of more than one segment of material. The topsheet 30 can be of different shapes, including rectangular, hourglass, or any other shape. The topsheet 30 can be suitably compliant, soft feeling, and non-irritating to the wearer's skin and can be the same as or less hydrophilic than the absorbent core 40 to permit body exudates to readily penetrate through to the absorbent core 40 and provide a relatively dry surface to the wearer.

The topsheet 30 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the topsheet 30. The topsheet 30 can include a woven fabric, a nonwoven fabric, a polymer film, a film-fabric laminate or the like, as well as combinations thereof. Examples of a nonwoven fabric can include spunbond fabric, meltblown fabric, conform fabric, carded web, bonded-carded web, bicomponent spunbond fabric, spunlace, or the like, as well as combinations thereof. The topsheet 30 need not be a unitary layer structure, and thus, can include more than one layer of fabrics, films, and/or webs, as well as combinations thereof. For example, the topsheet 30 can include a support layer and a projection layer that can be hydroentangled. The projection layer can include hollow projections, such as those disclosed in U.S. Patent Application Publication No. 2014/0121623 to Kirby et al. which is incorporated herein by reference in its entirety.

For example, the topsheet 30 can be composed of a meltblown or spunbond web of polyolefin fibers. Alternatively, the topsheet 30 can be a bonded-carded web composed of natural and/or synthetic fibers. The topsheet 30 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire topsheet 30 or it can be selectively applied to particular sections of the topsheet 30.

In an embodiment, a topsheet 30 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a topsheet 30 can be a spunbond substrate with a basis weight from about 10 or 12 to about 15 or 20 grams per square meter (gsm). In an embodiment, a topsheet 30 can be a 12 gsm spunbond-meltblown-spunbond substrate having 10% meltblown content applied between the two spunbond layers.

Although the topsheet 30 and the backsheet 32 can include elastomeric materials, it is contemplated that the topsheet 30 and the backsheet 32 can be composed of materials which are generally non-elastomeric. In an embodiment, the topsheet 30 can be stretchable, and more suitably elastic. In an embodiment, the topsheet 30 can be suitably stretchable and more suitably elastic in at least the lateral or circumferential direction of the absorbent article 10. In other aspects, the topsheet 30 can be stretchable, and more suitably elastic, in both the longitudinal and transverse directions 100, 106, respectively. Still further, the topsheet 30 can be further modified as by the addition of aperturing and/or embossing.

Containment Flaps:

In an embodiment, the absorbent article 10 can include a pair of containment flaps 80. The containment flaps 80 can be formed separately from the absorbent chassis 20 and attached to the chassis 20 or can be formed integral to the chassis 20. In some embodiments, the containment flaps 80 can be secured to the chassis 20 of the absorbent article 10 in a generally parallel, spaced relation with each other laterally inward of the leg openings to provide a barrier against the flow of body exudates. The containment flaps 80 can extend the entire length of the absorbent article 10 or a distance less than the entire length. The containment flaps 80 can be shorter or longer than depicted herein, including extending to the front waist edge 25a and the rear waist edge 25b. One containment flap 80a can be left of the longitudinal axis 100 and the other containment flap 80b can be right of the longitudinal axis 100. In an embodiment, the containment flaps 80 can extend generally in a longitudinal direction from the front waist region 21 of the absorbent article 10, through the crotch region 23 to the rear waist region 22 of the absorbent article 10. In some embodiments, the containment flaps 80 can extend in a direction substantially parallel to the longitudinal axis 100 of the absorbent article 10, however, in other embodiments, the containment flaps 80 can be curved, as is known in the art. In other embodiments, such as the absorbent article 10 in FIG. 11, the containment flaps 80 can be disposed on the absorbent panel 46 in the crotch region 23.

Each containment flap 80a and 80b has a proximal end 82 and a distal end 84. The proximal end 82 can be coupled to the chassis 20 via a barrier adhesive 85. For example, each containment flap 80 can be bonded to the topsheet 30 with a barrier adhesive 85 or the containment flaps 80 can be bonded to the backsheet 32 with a barrier adhesive 85 in embodiments where the topsheet 30 does not extend the full lateral width and/or full longitudinal length of the backsheet 32. Of course, the containment flaps 80 can be bonded to other components of the chassis 20 and can be bonded with other suitable means other than a barrier adhesive 85, such as, for example, thermal bonding. The containment flaps 80 can be constructed of a fibrous material which can be similar to the material forming the topsheet 30. Other conventional materials, such as polymer films, can also be employed.

It is contemplated that the containment flaps 80 can be of various configurations and shapes, and can be constructed by various methods. For example, the containment flaps 80 of FIGS. 1-6 and 10-11 depict a vertical containment flap 80a, 80b with a tack-down region 88 in both the front and rear waist regions 21, 22 where the distal ends 84 of each containment flap 80a, 80b is tacked down to the topsheet 30 towards or away from the longitudinal axis 100 of the absorbent article 10. However, the containment flaps 80 can include a tack-down region 88 where the distal end 84 of each of the containment flaps 80 is folded back upon itself and coupled to itself and the topsheet 30 in a "C-shape" configuration, as is known in the art and described in U.S. Pat. No. 5,895,382 to Robert L. Popp et al. As yet another alternative, it is contemplated that the containment flaps 80 could be constructed in a "T-shape" configuration, such as described in U.S. patent application Ser. No. 13/900,134 by Robert L. Popp et al., which published as U.S. Patent Application Publication 2014/0350504. Such a configuration can also include a tack-down region 88 in either or both of the front and rear waist regions 21, 22, respectively. Of course, other configurations of containment flaps 80 can be used in the absorbent article 10 and still remain within the scope of this disclosure.

The containment flaps 80 can include one or more flap elastic members 86 located in the distal ends 84 of the containment flaps 80. As shown in the figures, there are two containment flaps 80a and 80b each having a flap elastic member 86 including left flap elastic member 86a and right flap elastic member 86b. Each flap elastic member 86a and 86b is shown as having two flap elastic strands as depicted in FIGS. 1, 4B, 5 and 6. Suitable elastic materials for the flap elastic members 86 can include sheets, strands or ribbons of natural rubber, synthetic rubber, or thermoplastic elastomeric materials. Of course, while two elastic strands are shown forming the flap elastic members 86 in each containment flap 80a, 80b, it is contemplated that the containment flaps 80 can be configured with one or three or more elastic strands. Alternatively or additionally, the containment flaps 80 can be composed of a material exhibiting elastic properties itself such as an elastic film alone or in combination with nonwoven facing layers (not shown) to form a laminate. Desirably, the flap elastic members 86 are located adjacent the distal ends 84 of the containment flaps 80. Generally, the elastic members 86 will have a thickness of between about 460 and 800 decitex, alternatively, between about 600 and about 700 decitex. The elastic members 86 will have a tensile stress of between about 20 grams-force and about 80 grams-force, alternatively, between about 35 and about 45 grams-force. They can be made from a number of elastic materials including, but not limited to Lycra® elastic strands.

The flap elastic members 86, as illustrated in FIGS. 1, 4B, 5 and 6, can have two strands of elastomeric material extending longitudinally in the projection portion 96 of the containment flaps 80, in generally parallel, spaced relation with each other. The elastic members 86 can be attached to the containment flaps 80 while in an elastically contractible condition such that contraction of the strands gathers and shortens, in the longitudinal direction, the material of the containment flaps 80 adjacent the distal ends 84. As a result, the elastic members 86 can bias the distal ends 84 of the containment flaps 80 to extend away from the body facing surface 31 of the topsheet 30 in a generally upright orientation of the containment flaps 80, especially in the crotch region 23 of the absorbent article 10, when the absorbent article 10 is in a relaxed configuration.

During manufacture of the containment flaps 80 at least a portion of the flap elastic members 86 can be bonded to the containment flaps 80 while the elastic members 86 are elongated. The percent elongation of the elastic members 86 can be, for example, about 110% to about 350%. The elastic members 86 can be coated with adhesive while elongated to a specified length prior to attaching to the elastic members 86 to the containment flaps 80. In a stretched condition, the length of the elastic members 86 which have adhesive coupled thereto can provide an active flap elastic region in the area of the distal ends 84 between the tack down regions 88 which will gather upon relaxation of the absorbent article 10. In this exemplary method of bonding the elastic members 86 to the containment flaps 80, the portion of the elastic members 86 not coated with adhesive will retract after the elastic members 86 and the absorbent article 10 are cut in manufacturing to form an individual absorbent article 10. As noted above, the relaxing of the elastic members 86 when the absorbent article 10 is in a relaxed condition can cause each containment flap 80a, 80b to gather and cause the distal ends 84 of each containment flap 80a, 80b to extend away from the body facing surface 20a of the chassis 20 (e.g., the body facing surface 44 of the absorbent core 40 or the body facing surface 31 of the topsheet 30, as depicted in FIG. 4B. In addition to adhesives, the elastic members 86 can be bonded to the containment flaps 80 in various other ways including thermal bonding or combinations of adhesive and thermal bonding.

Leg Elastics:

To increase leakage protection, the chassis 20 is fitted with leg elastic members 70 about the leg openings in the absorbent article 10. The leg elastic members 70 include a left leg elastic member 70a and a right leg elastic member 70b. Leg elastic members 70a, 70b can be secured to the backsheet 32, such as by being bonded thereto by laminate adhesive, generally laterally inward of the longitudinal side edges, 24a and 24b, of the absorbent article 10. The leg elastic members 70a, 70b can form elasticized leg cuffs that further help to contain body exudates. In an embodiment, the leg elastic members 70a, 70b may be disposed between the topsheet 30 and the backsheet 32 and, alternatively, between the body facing layer 34 and garment facing layer 36 of the backsheet 32 or between other layers of the absorbent article 10. The leg elastic members 70a, 70b can comprise one or more elastic components near each longitudinal side edge 24a, 24b of the absorbent article 10. For example, the leg elastic members 70a, 70b as illustrated herein each include two elastic strands. A wide variety of elastic materials may be used for the leg elastic members 70a, 70b. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Additionally, it is contemplated that the leg elastic members 70a, 70b can be formed with the containment flaps 80, and then attached to the chassis 20 in some embodiments.

Waist Containment Member:

In an embodiment, the absorbent article 10 can have one or more waist containment members 92. FIGS. 1, 4A, 4B, 6 and 11 depict an absorbent article 10 with an embodiment of a waist containment member 92.

The waist containment member 92 can be disposed in the rear waist region 22. The waist containment member 92 can help contain and/or absorb body exudates, especially low viscosity fecal matter, and as such, can be preferred to be in the rear waist region 22. In some embodiments, the absorbent article 10 can have a waist containment member 92 disposed in the front waist region 21. A waist containment member 92 in the front waist region 21 can help contain and/or absorb body exudates, such as urine, in the front waist region 21. Although not as prevalent as in the rear waist region 22, in some circumstances, fecal material may also spread to the front waist region 21, and thus, a waist containment member 92 disposed in the front waist region 21 can help contain and/or absorb body exudates as well. In other embodiments, the absorbent article 10 can have a waist containment member 92 in both the rear waist region 22 and the front waist region 21.

In some embodiments, the waist containment member 92 can be disposed on the body facing surface 44 of the absorbent core 40. In some embodiments, such as in embodiments illustrated in FIGS. 1, 4A, 4B and 6, the waist containment member 92 can be disposed on the body facing surface 31 of the topsheet 30. However, in some embodiments, such as the absorbent article 10 in FIG. 11, the waist containment member 92 can be disposed on a body facing surface of the rear waist panel 29.

Referring to FIGS. 1 and 11, the waist containment member 92 can include a first longitudinal side edge 92a and a second longitudinal side edge 92b. The first longitudinal side edge 92a can be opposite from the second longitudinal side edge 92b. In some embodiments, the first longitudinal side edge 92a can substantially align with the left side edge 24a of the absorbent article 10. Similarly, in some embodiments, the second longitudinal side edge 92b can align with the right side edge 24b of the absorbent article 10. Each of the longitudinal side edges 92a and 92b may include a tack down region 87 to attach the waist containment member 92 to a body facing surface 20a of the chassis 20.

The waist containment member 92 can also include a proximal portion 92c and a distal portion 92d. The proximal portion 92c can be coupled to a body facing surface 20a of the absorbent article 10 such as the body facing surface 31 of the topsheet 30 whereas the distal portion 92d of the waist containment member 92 can be free to move with respect to the chassis 20 and the absorbent core 40 when the absorbent article 10 is in the relaxed configuration.

The proximal portion 92c can be coupled to the chassis 20 with an adhesive. In some embodiments, such as the absorbent article 10 in FIG. 11, the proximal portion 92c of the waist containment member 92 can be coupled to the body facing surface 29a of the rear waist panel 29.

Due to the fact that at least a portion or all of the distal portion 92d of the waist containment member 92 can freely move with respect to the absorbent core 40 when the absorbent article 10, is in the relaxed configuration, the distal portion 92d can help provide a containment pocket 99 when the absorbent article 10 is in the relaxed configuration. The containment pocket 99 can help provide a barrier to contain and/or can help absorb body exudates.

The waist containment member 92 can include at least one elastic member 92e. In some embodiments, the waist containment member 92 can include multiple elastic members 92e. A wide variety of elastic materials may be used for the elastic member(s) 92e in the waist containment member 92. Suitable elastic materials can include sheets, strands or ribbons of natural rubber, synthetic rubber, thermoplastic elastomeric materials, or elastic foams such as are described and used with respect to the flap elastic members 86 and the leg elastic members 70.

The main body of the waist containment member 92 can be made from a variety of materials including fibrous nonwoven webs, polymeric films and combinations of the foregoing including laminates of various types of fibrous nonwoven webs and polymeric films. Typically, it is desirable that the material used to make the waist containment member 92 be vapor permeable, soft and non-irritating as its body facing surface will be in contact with the skin of the wearer. As a result, materials suitable for use as the topsheet 30 and containment flaps 80 are also suitable for use as the containment member 92.

Backsheet:

The backsheet 32 and/or portions thereof can be breathable and/or liquid impermeable. The backsheet 32 and/or portions thereof can be elastic, stretchable, or non-stretchable. The backsheet 32 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the backsheet 32 can be constructed of a microporous polymeric film, such as polyethylene or polypropylene.

In an embodiment, the backsheet 32 can be a single layer of a liquid impermeable material, such as a polymeric film. In an embodiment, the backsheet 32 can be suitably stretchable, and more suitably elastic, in at least the lateral direction 106 of the absorbent article 10. In an embodiment, the backsheet 32 can be stretchable, and more suitably elastic, in both the lateral 106 and the longitudinal 100 directions. In an embodiment, the backsheet 32 can be a multi-layered laminate in which at least one of the layers is liquid impermeable. In some embodiments, the backsheet 32 can be a two layer construction, including an body facing layer 34 and an garment facing layer 36 which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The garment facing layer 36 of the backsheet 32 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® nonwoven or equivalent. Another example of material suitable for use as a garment facing layer 36 of a backsheet 32 can be a 20 gsm spunbond polypropylene non-woven web. The garment facing layer 36 may also be constructed of the same materials from which the topsheet 30 can be constructed as described herein.

The liquid impermeable body facing layer 34 of the backsheet 32 (or the liquid impermeable backsheet 32 where the backsheet 32 is of a single-layer construction) can be either vapor permeable (i.e., "breathable") or vapor impermeable. The liquid impermeable body facing layer 34 (or the liquid impermeable backsheet 32 where the backsheet 32 is of a single-layer construction) can be manufactured from a thin plastic film to inhibit liquid body exudates from leaking out of the absorbent article 10 and wetting articles, such as bed sheets and clothing, as well as the wearer and caregiver.

In some embodiments, where the backsheet 32 is of a single layer construction, it can be embossed and/or matte finished to provide a more cloth-like texture or appearance. The backsheet 32 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Absorbent Core:

An absorbent core 40 can be positioned between the topsheet 30 and the backsheet 34. The absorbent core 40 can generally be any single layer structure or combination of layered components, which can demonstrate some level of compressibility, conformability, be non-irritating to a wearer's skin, and capable of absorbing and retaining liquids and other body exudates. Additionally, the absorbent core 40 can provide additional capacity to absorb and retain body exudates such as urine and feces. In various embodiments, the absorbent core 40 can be formed from a variety of different materials and can contain any number of desired layers. For example, the absorbent core 40 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of a wood pulp fluff can be identified with the trade designation NB 416, available from Weyerhaeuser Corp., and is a bleached, highly absorbent wood pulp containing primarily soft wood fibers.

In various embodiments, if desired, the absorbent core 40 can include a high absorbency material also referred to as a superabsorbent material. Examples of suitable superabsorbent material can include poly(acrylic acid), poly(methacrylic acid), poly(acrylamide), poly(vinyl ether), maleic anhydride copolymers with vinyl ethers and α-olefins, poly(vinyl pyrrolidone), poly(vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 40 in any amount as desired.

Regardless of the combination of absorbent materials used in the absorbent core 40, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A conform nonwoven material can also be employed. Methods and apparatus for carrying out such techniques are well known in the art.

The shape of the absorbent core 40 can vary as desired and can comprise any one of various shapes including, but not limited to, triangular, rectangular, dog-bone and elliptical shapes. In various embodiments, the absorbent core 40 can have a shape that generally corresponds with the overall shape of the absorbent article 10. The dimensions of the absorbent core 40 can be substantially similar to those of the absorbent article 10, however, it will be appreciated that the dimensions of the absorbent core 40 while similar, will often be less than those of the overall absorbent article 10, in order to be adequately contained therein.

By way of example, suitable materials and/or structures for the absorbent core 40 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al., each of which is hereby incorporated by reference hereto in its entirety.

As described above, in various embodiments, an absorbent core 40 can be a single layer structure and can include, for example, a matrix of cellulosic fluff and superabsorbent material. In various embodiments, an absorbent core 40 can have at least one and if desired two or more layers of material, such as, for example, a body facing layer and a garment facing layer. In various embodiments, the two layers can be identical to each other. In various embodiments, the two layers can be different from each other. In such embodiments, the two layers can provide the absorbent article 10 with different absorption properties as deemed suitable. In various embodiments, the body facing layer of the absorbent core 40 may be constructed of an airlaid material and the garment facing layer of the absorbent core 40 may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

As a general rule, the high-absorbency superabsorbent material may be present in the absorbent core 40 in an amount of from about 5 to about 95 weight percent and desirably from about 10 to about 60 weight percent based on the total weight of the absorbent core 40. The distribution of the high-absorbency material within the different portions of the absorbent core 40 can vary depending upon the intended end use of the absorbent core 40.

Channels and Shaping Elastic Members:

A desired feature of the absorbent article 10 is to provide a structure that will allow air circulation about the genital area of the wearer. To this end, the absorbent article 10 is designed to cause the chassis 20 to have a more pronounced convex curvature away from the genitalia of the wearer and the resultant insult area to the product. Due to the differences in male and female anatomy, the male insult area 120 is located more towards the front waist region 21 than the female insult area 121. See FIGS. 3A and 3B. This is why it is often desirable to manufacture and market differently designed absorbent articles for males versus females. However, when this is not feasible, absorbent article manufacturers will produce what are termed unisex products with a unisex target area 122 which is a compromise relative to the male insult area 120 and the female insult area 121. See FIG. 3C. Through the use of channels 50, shaping elastic members 60 (to be described in more detail below) and the containment flaps 80 as well as the manner in which the article 10 is folded, a resultant product is created which allows the insulted area (120, 121, 122) of the absorbent core 40 to be distanced from the wearer. It is believed that this extended convex design is more advantageous from a skin health perspective because it results in the wetted insult area (120, 121, 122) of the absorbent article 10 being more distanced from the skin of the wearer which is a positive benefit relative to skin irritation caused by prolonged contact with the wet product. It also provides a better fit relative to the torso of the wearer.

Turning to FIGS. 1-4, as with the overall absorbent article 10, the absorbent core 40 is bisected in the transverse direction by the longitudinal axis 100 into a left region 102 and a right region 104. The overall absorbent article 10 as well as the absorbent core 40 is also bisected in the longitudinal direction by the transverse axis 106 into a front region 108 and a rear region 110. The crotch region 23 covers the approximate middle one-third of the absorbent core 40, the front waist region 21 covers the approximate front one-third of the absorbent core 40 and the rear waist region 22 covers the approximate rear one-third of the absorbent core 40 relative to the longitudinal direction 100 of the article 10. It is contemplated, however, that this proportions may be varied depending on the size and type of product as well as the side of the wearer.

To facilitate the overall ability of the absorbent article 40 to take on the generally convex shape P as desired by the present invention, the absorbent core 40 defines at least one or more openings 50, also referred to as channels 50, extending through the thickness 43 of the absorbent core 40 which are devoid of absorbent core material. As shown in the Figures, each of the plurality of channels 50 (in this case, two channels 50a and 50b) has a channel front end 51, a channel rear end 52, a channel left side edge 53 and a channel right side edge 54. Each opening 50 further has a channel length 55 as measured between the channel front end 51 and the channel rear end 52. Each opening or channel 50 has a channel width as measured between the channel left side edge 53 and the channel right side edge 54. The number and location of the channels may be varied.

These channels 50 provide several functions. First, they reduce the overall weight and density of the absorbent core 40 in the region in which they are located, thus increasing the flexibility of the core 40 and the absorbent article 10 as a whole. This helps in allowing the article 10 as a whole take on a more pronounced convex shape. Second, the channels 50 increase the lateral compressibility of the absorbent core 40 in the crotch region 43. Third, they provide expansion room for the absorbent core 40 to expand as it absorbs body exudates while reducing the lateral stresses on the absorbent core 40 due to the expansion of the absorbent core material as a result of being wetted. As explained above, one desired attribute of the resultant product is for the absorbent core 40 and the absorbent article 10 as a whole to remain distanced from the skin of the wearer. The channels 50 allow for increased expansion of the absorbent core 40 in the lateral direction along the transverse axis 106 thereby alleviating to some degree the vertical expansion of the absorbent core 40 in the vertical direction along the z-directional axis 112.

The channels 50 desirably extend all the way through the absorbent core 40 in the Z direction 112 thereby creating openings or voids in the core 40. In alternate embodiments (not shown), however, the channels 50 can be areas of reduced material due to removal of a portion of the absorbent core material in this area. Alternatively, or additionally, the channel areas can be areas of reduced thickness due to the compression of the absorbent core material in this area by embossing or other compression means known to those of ordinary skill in the art. Still further, though not shown, such embossments in the absorbent core 40 can be used in addition to the channels 50 already present in the absorbent core 40. The length, width, depth and shape of such embossments can vary. Generally, these areas of reduced thickness due to removal and/or compression of material will have a length of about 50 mm to about 300 mm, alternatively, about 70 mm to about 100 mm and still further between about 80 mm and about 9 mm. The width of these areas of reduced thickness will range from about 2 mm and about 7 mm, alternatively, between about 3 mm and about 5 mm.

Each of the channels 50 can be of the same shape or of different shapes from one another. They can also vary in length and width as well as number. They can be long and thin such as is shown in FIGS. 1-3 but they can also be a series of separate shorter channels (not shown) running parallel or non-parallel to one another. They can be square, elliptical, round, multisided, straight or curved or any combination of the foregoing. They generally have a major axis that is generally in the direction of the longitudinal axis 100 and a minor axis that is generally in the direction of the transverse axis 106. They can run the entire longitudinal length of the absorbent core 40 in which case the absorbent core 40 will be divided in the transverse direction into multiple generally parallel and separate absorbent cores. Alternatively, they can be shorter than the overall length of the absorbent core 40. The major axis and thus the length 55 of a channel 50 is the longest line that can be drawn within the channel 50 without intersecting a side wall 53, 54 of the channel 50. As a result, this line may be straight or curved or both. The minor axis and thus the width of a channel 50 is any line that can be drawn perpendicular to the line of the major axis at any point along the major axis of the channel. If a channel 50 is made up of a series of smaller channels with sections of absorbent core material in between the smaller channels 50, the length of the channels can be regarded as the overall length of the series of channels including the intervening absorbent core material.

Generally, the individual channels 50 will have a length 55 from about 50 mm and 300 mm, alternatively, between about 120 mm and about 160 mm and still further, between about 130 mm and about 140 mm. Dimensions outside this range can also be used.

Generally, the width of each channel will be between about 5 mm and about 15 mm, alternatively, between about 8 mm and about 12 mm. The width is measured from the channel left side edge 53 to the channel right sight edge 54. Dimensions outside this range can also be used.

The spacing between the channels 50, and in particular from the interior edge of one channel and the interior edge of the other channel (right side edge 54 of channel 50a and left side edge 54 or channel 50b) will range between about 40 mm and about 60 mm, alternatively, between about 44 mm and about 48 mm. Dimensions outside this range can also be used.

The channel front end 51 is spaced from the front waist edge 25a by a distance of about 100 mm to about 220 mm, more particularly about 140 mm to about 160 mm from the front waist edge 25a. Dimensions outside this range can also be used depending on the size of the overall absorbent article.

In addition to the channels 50, the absorbent article 10 is also fitted with what are termed shaping elastic members 60 which are located in the transverse direction 106 laterally outboard of the absorbent core longitudinal side edges 42a and 42b. See FIGS. 1-3. FIG. 4B is a cross-section of FIG. 1B and is representative of all the respective male, female and unisex versions of the absorbent article 10 along the transverse axis 106. As shown in FIG. 4B, the shaping elastic members 60 are a pair including a left side shaping elastic member 60a and a right side shaping elastic member 60b which run generally in the longitudinal direction. These shaping elastic members 60a and 60b can be made from and installed in the same fashion as described above with respect to the containment flap elastic members 86 and the leg elastic members 70. Each shaping elastic member 60a and 60b has a shaping elastic member front end 62 and a shaping elastic member rear end 64 which define a shaping elastic member length 66 therebetween. Generally it is desirable that the shaping elastic members 60 have a length 66 of about 50 mm to about 400 mm, alternatively, about 100 mm to about 350 mm and still further about 140 mm to about 230 mm.

In FIG. 4B it can be seen that the shaping elastic members, designated 60a (left side) and 60b (right side) are positioned between the body facing layer 34 and the garment facing layer 36 of the backsheet 32. It has been found that this is a desirable location from a manufacturing perspective. However, the shaping elastic members 60 can be located between other components of the absorbent article 10 but it is desirable that they be located outboard of the longitudinal side edges 41a and 41b of the absorbent core 40. When a core wrap 57 is used to enclose the absorbent core 40, it is desirable that the shaping elastic members 60 be located outside the core wrap 57. It is also desirable that the shaping elastic members 60 not extend under any portion of the absorbent core 40 so that the lifting forces are not applied directly to any portion of the absorbent core 40. The shaping elastic members 60 shown in the Figures are straight but curved designs may also be used.

Figure 6:
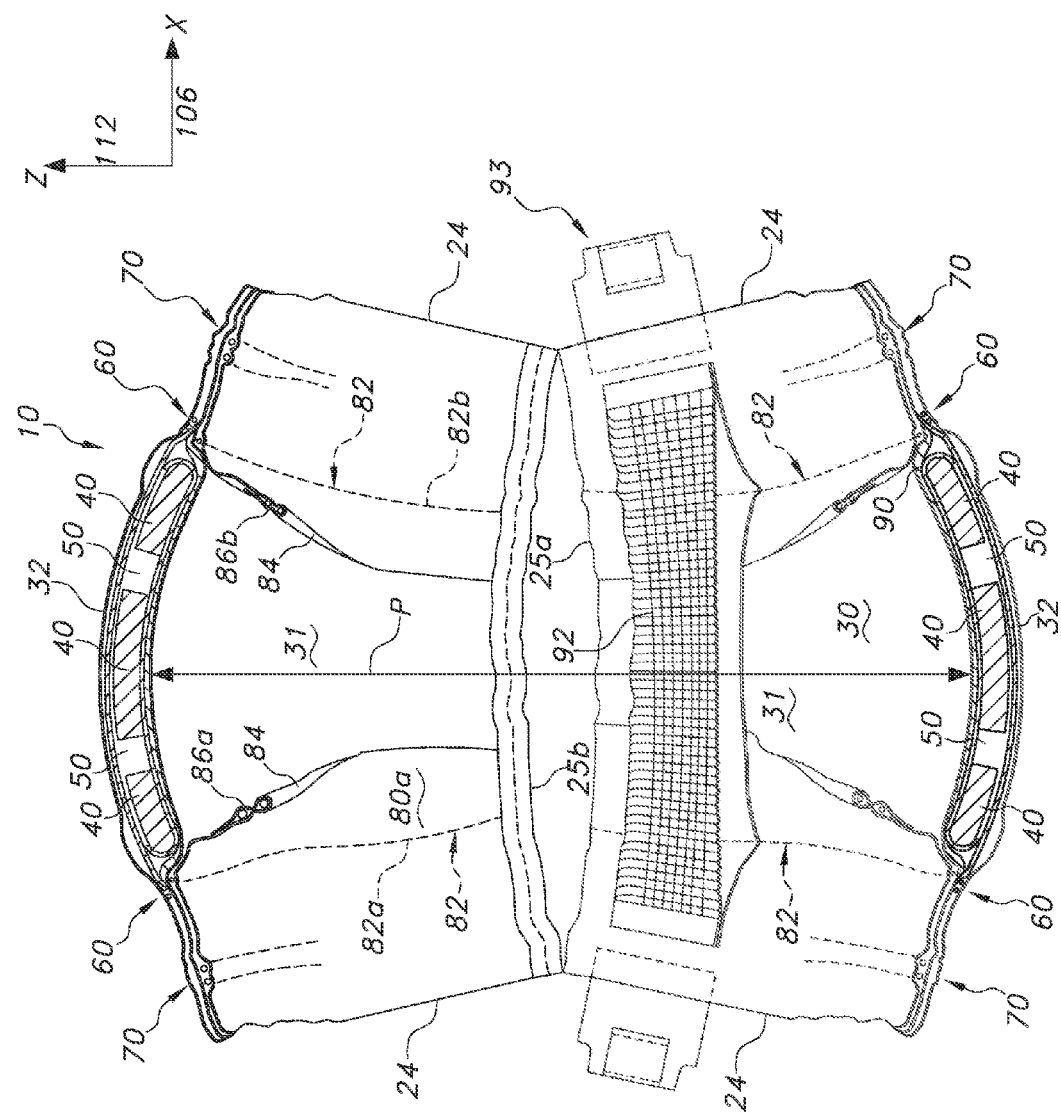
FIG. 6 is cross-sectional end view of the absorbent article of FIG. 1A along line 6-6 of FIG. 4A.

As shown in FIGS. 4B, 5 and 6 the shaping elastic members 60a and 60b are located in vertical juxtaposition with the proximal ends 82 of the containment flaps 80. By "vertical juxtaposition" it is meant that a vertical line 130 can be drawn that passes through the point of attachment of the proximal ends 82 of the containment flaps (80a or 80b) to the chassis 20 and the midpoint of the respective shaping elastic member 60a or 60b. As a result, the proximal end 82 of the containment flap 80 and the shaping elastic member 60 are considered to be in vertical juxtaposition and alignment if there is no more than a 20 millimeter, more preferably no more than a 10 millimeter offset from a vertical line 130 drawn through one or the other of the proximal end 82 of the containment flap 80 and the midpoint of the shaping elastic member 60. In this regard, the "midpoint" of the elastic member is the lateral center point (along the transverse direction 106) of the width of the elastic member 60 when the elastic member is a single element such as a single elastic strand or ribbon, or the midpoint of the collective width of members 60 when there are multiple elements making up the shaping elastic member 60. Thus, for example, with respect to the pair of elastic strands in each of the shaping elastic members 60a or 60b show in FIG. 4B, the midpoint for each would be the point centered laterally between the two elastic strands of 60a or 60b relative to respective proximal ends 82a and 82b of the containment flaps 80. The proximal end 82 (82a, 82b) is the location of attachment of the containment flap 80 to the chassis 20. In the case of the embodiments shown in FIGS. 4B, 5 and 6, this point of attachment of the proximal end 82 of the containment flap 80 is the point of attachment to the body facing surface 31 of the topsheet 30 adjacent the adhesive 85. See FIG. 5. At the location of the adhesive 85, the remaining inboard portion (towards the longitudinal axis or centerline 100) of the containment flap 80 (the distal end or portion 84) is free of attachment to the chassis 20.

In FIG. 4B, due to the shaping elastic members 60 being located in the backsheet 32 between the body facing layer 34 and garment facing layer 36, the shaping elastics 60 are isolated from and located below the lateral plane of the bottom side of the absorbent core 40. It is believed that this is the most advantageous location for the shaping elastic members 60 as it allows the shaping elastic members 60 to act on the overall absorbent article 10 and not just the absorbent core 40. Furthermore, this location facilitates manufacture of the product as well. It is possible, however, to move the location of the shaping elastic members 60 vertically upward while still maintaining the vertical juxtaposition with the proximal ends 82 of the containment flaps 80. For example, the shaping elastic members 60 may be located between the backsheet 32 and the topsheet 30 or, when the article 10 employs an acquisition layer 90, the shaping elastic members 60 may be located between the backsheet 32 and the acquisition layer 90 or between the acquisition layer 90 and the topsheet 30. The attachment of the shaping elastics 60 to the adjacent layers of material (such as the topsheet 30, backsheet 32, including the body facing layer 34 and garment facing layer 36, acquisition layer 90 or any other layer) can be accomplished using the same techniques and materials as discussed herein with respect to the leg elastic members 70, flap elastic members 86 and waist containment elastic members 92e including, but not limited to, adhesives and thermal bonding.

Laterally, in the transverse direction 106, the shaping elastics members 60 are positioned between the longitudinal side edges 41 (41a, 41b) of the absorbent core 40 and the leg elastic members 70. Generally, the shaping elastic members 60 should be spaced laterally outboard (outboard being a spatial relationship relative to the longitudinal axis 100 of the absorbent article 10) of the absorbent core 40 and any associated core wrap 57. In this way there is less likelihood of the absorbent structure being damaged by the shaping elastic members 60. In this regard, it is desirable that the shaping elastic members 60 be positioned laterally outboard from the longitudinal side edges 41a and 41b of the absorbent core 40 by a distance of from about 5 mm to about 40 mm, alternatively from about 5 mm to about 20 mm.

Figure 4A:
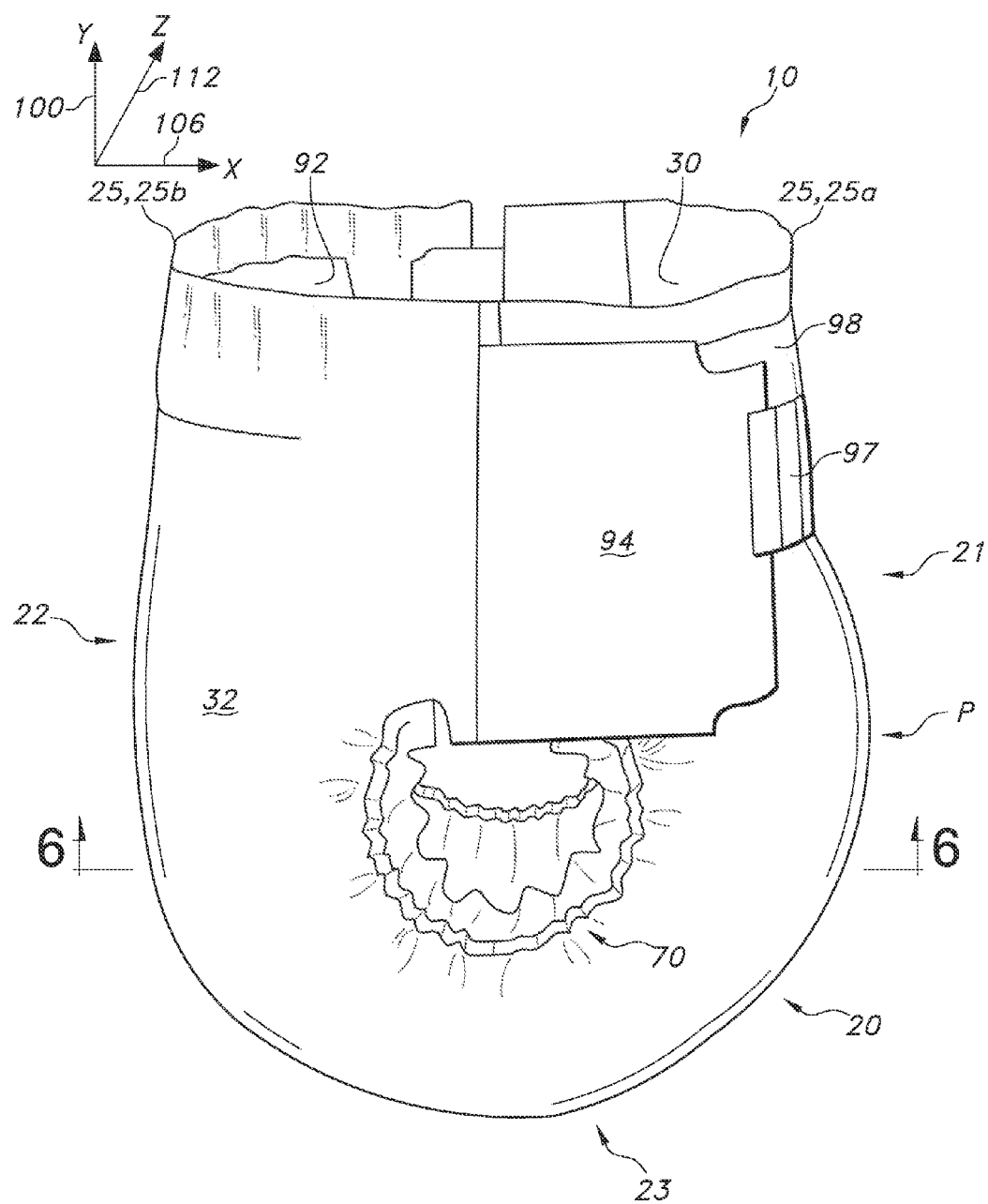
FIG. 4A is a perspective side view of an exemplary embodiment of male version of the absorbent article of FIG. 1A, showing the enhanced convex or outward curvature of the chassis according to the present invention.

The tension the shaping elastic members 60 apply to the article 10 should be sufficient to achieve the type of pronounce convex curvature that is illustrated in FIGS. 4A and 6 and in the photographs of FIGS. 7B-1, 7C-1, 8B-1, 8C-1, 9B-1 and 9C-1. In these Figures, the area of pronounced convex curvature is referenced as area "P". While the shaping elastic members 60 provide the main tension and force needed to create the exaggerated convex outward shape of the absorbent article 10, the creation of this shape can be supplemented by the tensional forces applied to the absorbent article 10 by way of the leg elastic members 70 and the flap elastic members 86. Generally, however, it is desirable that the tension forces applied by the shaping elastic members 60 be less than the tension forces applied by the leg elastic members 70. It is also desirable that the tension forces applied by the shaping elastic members 60 be less than the tension forces applied by the flap elastic members 86. Generally, the shaping elastic members 60 should supply a tensile stress from about 20 grams force (gf) to about 80 gf, alternatively from about 30 gf to about 60 gf, and still further, from about 35 gf to about 45 gf. This tensile stress should be determined as to the portion of the shaping elastic members 60 located in the crotch region 23 of the absorbent article 10. If the shaping elastic member 60 comprises a single elastic strand of material, this value is determined as to this individual strand located on one side of the longitudinal axis 100. If two or more elastic strands or a composite material is used, it should be for the total elastic strands or entire composite material on one side of the longitudinal axis 100. Generally, the degree of tensile stress will depend on both the decitex rating of the elastic strands and the degree of elongation applied to the strand(s) during its attachment to the chassis 20 of the absorbent article 10. In the context of absorbent articles, decitex ratings of between about 460 and about 800 are desirable when using Lycra®-based elastic strands.

Figure 3A:
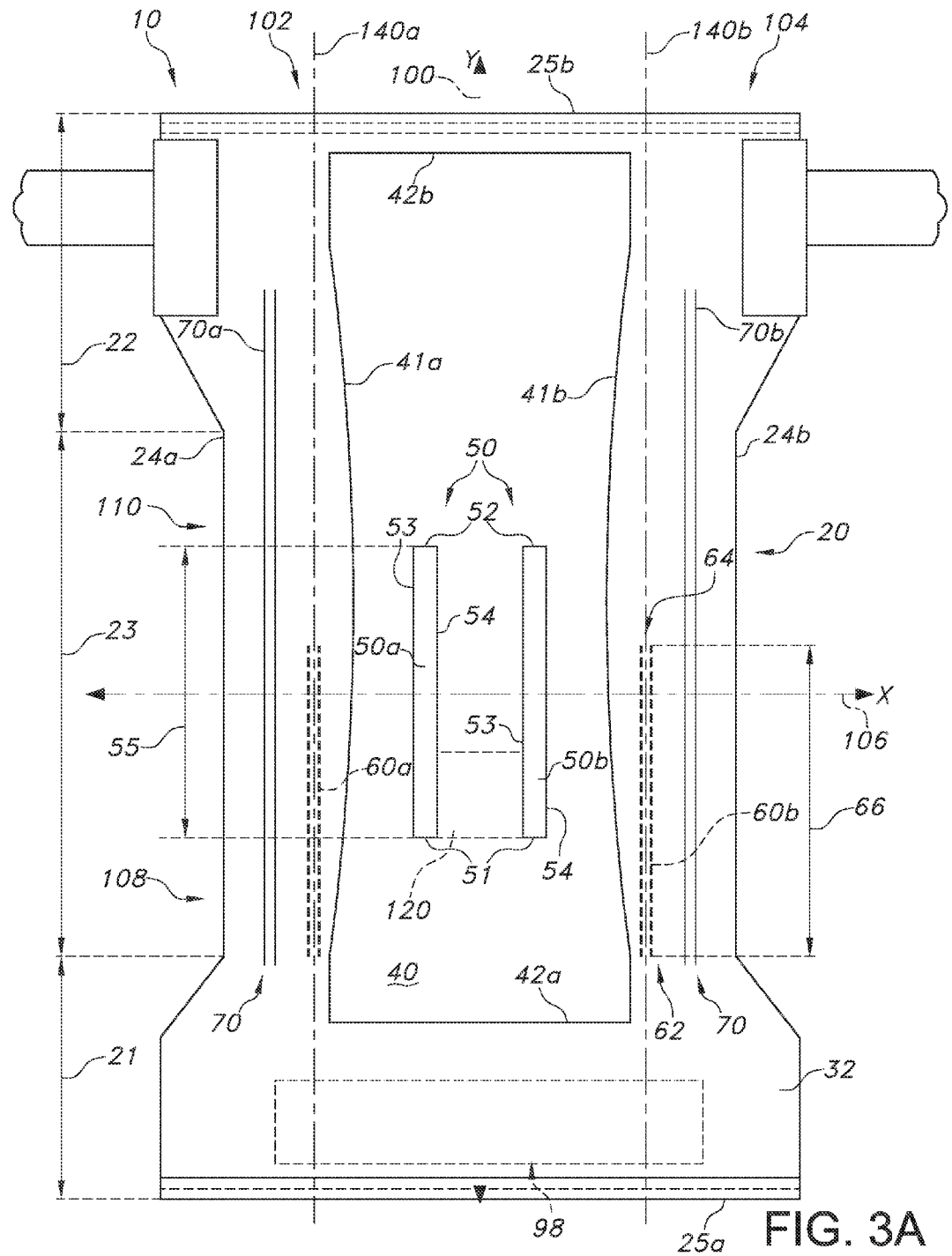
FIG. 3A is a partial top plan view of the absorbent article of FIG. 1A with the layers above the absorbent core removed including the core wrap, any optional acquisition layer and the topsheet.
Figure 3B:
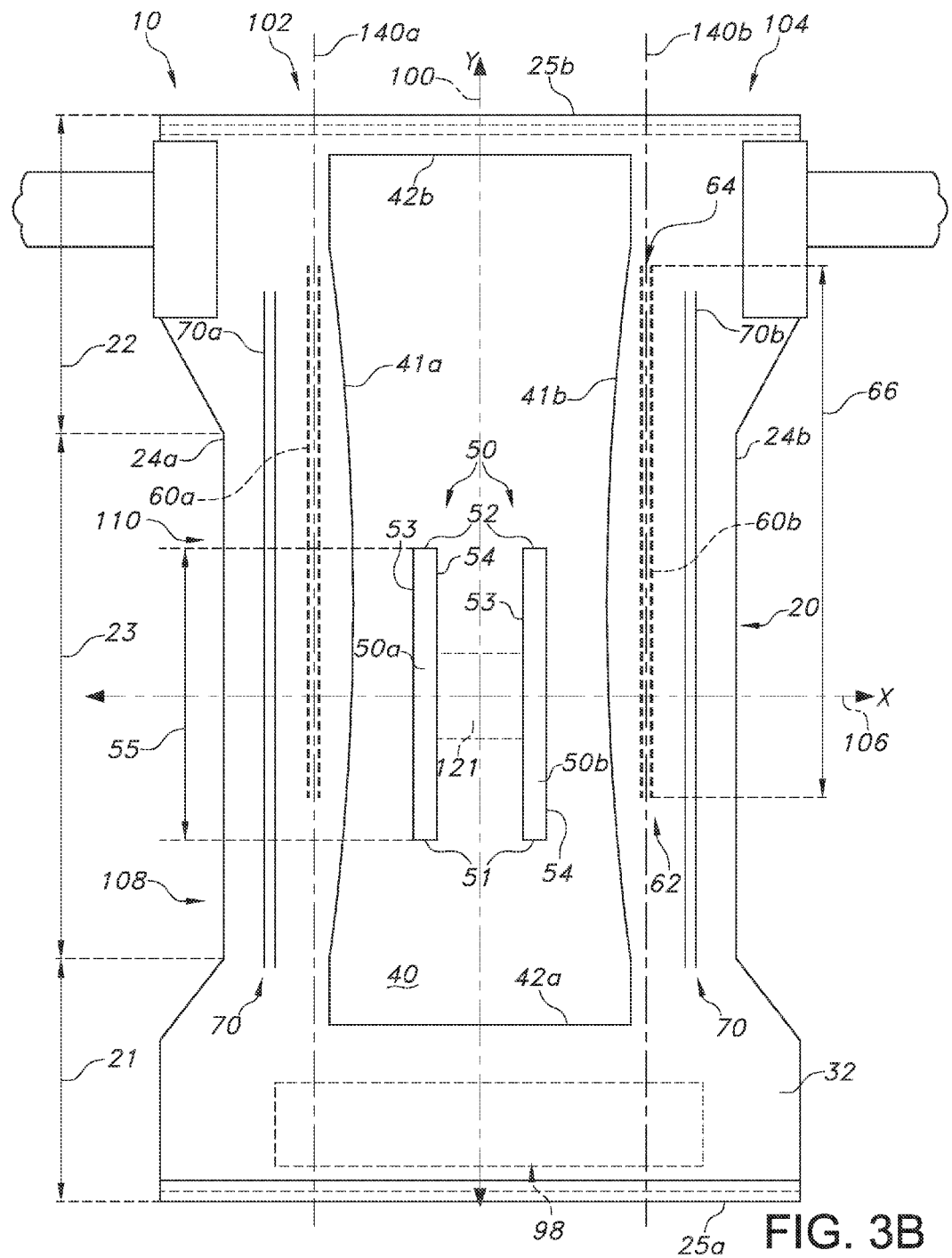
FIG. 3B is a partial top plan view of the absorbent article of FIG. 1B with the layers above the absorbent core removed including the core wrap, any optional acquisition layer and the topsheet.
Figure 3C:
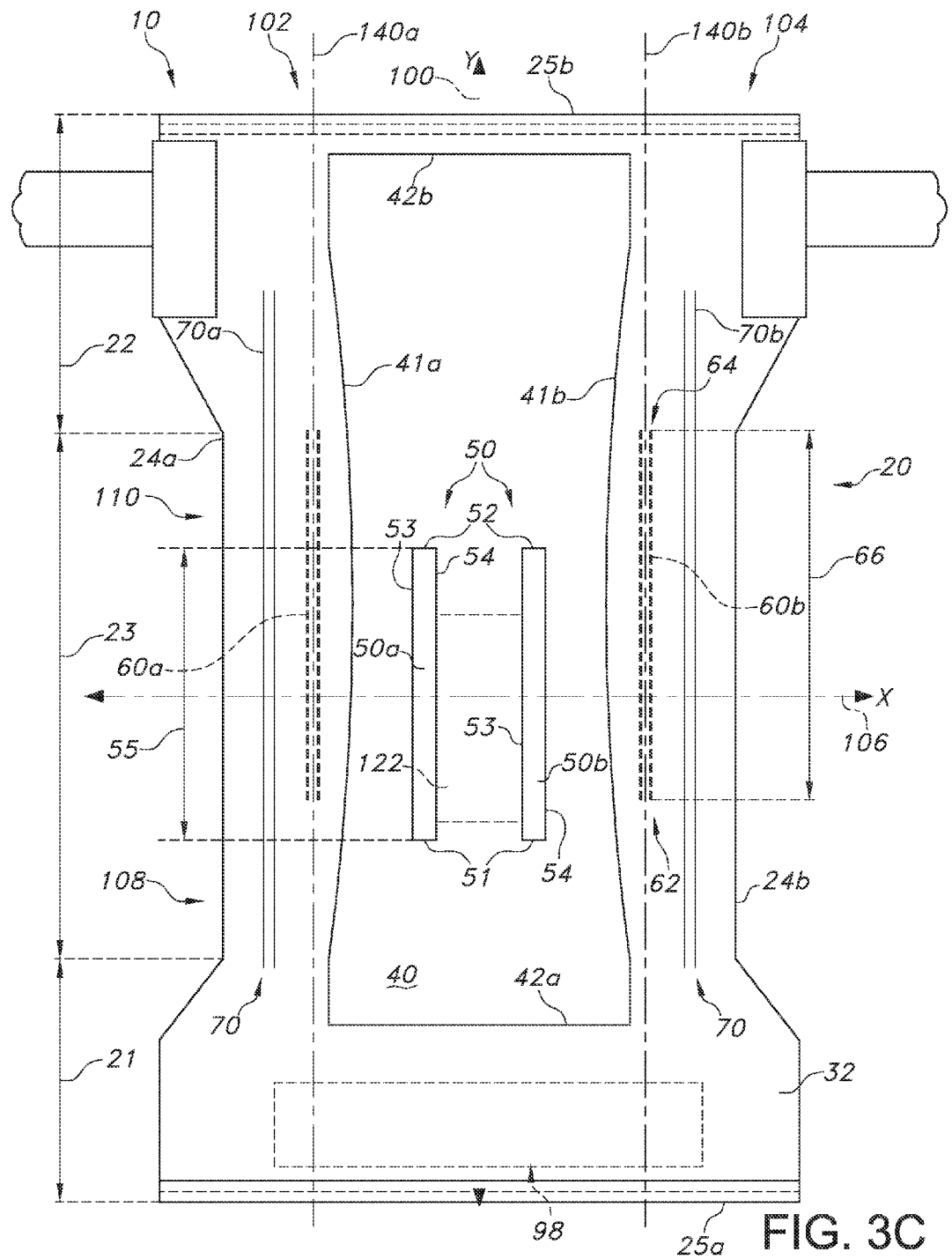
FIG. 3C is a partial top plan view of the absorbent article of FIG. 1C with the layers above the absorbent core removed including the core wrap, any optional acquisition layer and the topsheet.

Turning to FIGS. 1 and 3, there are shown three versions of the absorbent article 10 according to the present invention. FIGS. 1A and 3A depict a male version of the present invention. FIGS. 1B and 3B depict a female version of the present invention and FIGS. 1C and 3C depict a unisex version of the present invention. In each of the embodiments there is shown a first channel 50a and a second channel 50b spaced equidistant from the longitudinal axis 100. While this is representative of a preferred embodiment, other combinations of sizes, shapes and numbers of channels are also possible. Channel 50a is located in the left region 102 and channel 50b is located in the right region 104. Each of the channels 50 in all three embodiments is skewed towards the front waist region 21 of the absorbent article 40 and therefore is contained in the crotch region 23 and the front waist region 21 but desirably is not located in the rear waist region 22. As a result, relative to the overall length of the absorbent core 40, the channels 50a and 50b are located in the approximate middle one-third and the front one-third of the absorbent core 40. Other locations are also contemplated to be within the scope of the present invention.

The location of the shaping elastic members 60 vary from the male version (FIG. 1A, 3A), the female version (FIG. 1B, 3B) and the unisex version (FIG. 1C, 3C) relative to the target zones 120, 121, and 122 respectively for insulting by body exudates and in particular urine. In the male version, the shaping elastic members 60 are skewed more towards the front of the absorbent article 10 so as to have the convex curvature P be aligned with the target zone 120. As a result, it is desired that in this configuration, the outward, convex shape P of the absorbent core 40 and the overall absorbent article 10 be more pronounced in the forward portion of the crotch region 23 of the absorbent core 40 towards the front waist region 21. To create this effect, the front end 51 and the rear end 52 of the channels 50 are respectively forward of the front end 62 and the rear end 64 of the shaping elastics members 60. By "forward" it is meant that the respective element of the article 10 is closer to the front waist edge 25*a*. In the male embodiment of FIG. 1A, 3A, the shaping elastics members 60 will be predominantly in the front half or region 108 of the article 10. By "predominantly" as to the male, female and unisex versions of the absorbent article 10 it is meant that from about 60 to about 100 percent of the length 66 of the shaping elastic members 60, more particularly between about 80 and about 100 percent of the length 66 of the shaping elastic members 60 is located forward of the transverse axis 106.

In an embodiment of the male version of the absorbent article 10 it is desirable that the length 55 of the channels 50 be generally equal to the length 66 of the shaping elastic members 60. By "generally equal" it is meant that the respective lengths 55 and 66 are within about 80 to 100 percent of one another, more particularly within about 90 and 100 percent of one another. As a result, the length 55 of the channels 50 can be larger, smaller or equal to the length 66 of the shaping elastic members 60.

In an embodiment of the male version of the absorbent article 10 the length 55 of the channels 50 can range from about 50 mm to about 300 mm and more particularly from about 120 mm to about 160 mm and still further from about 130 mm to about 140 mm. In an embodiment, the length of the shaping elastic members 60 can range from about 50 mm to about 300 mm and more particularly from about 100 mm to about 200 mm and still further from about 140 mm to about 170 mm.

In the female version (FIGS. 1B and 3B), the shaping elastic members 60 are skewed more towards the rear of the absorbent article 10. As a result, it is desired that in this configuration, the outward, convex shape P of the absorbent core 40 is more pronounced in the central portion of the crotch region 23 of the absorbent core 40 so as to be aligned with the target zone 121. To create this effect, the front end 62 and the rear end 64 of the shaping elastics members 60 are respectively rearward of the front end 51 and the rear end 52 of the channels 50. By "rearward" it is meant that the respective element of the article 10 is closer to the rear waist edge 25*b*/chassis rear end edge than is the other element. In the embodiment of FIG. 1B, 3B, the shaping elastics members 60 will be predominantly in the rear half or region 110 of the article 10. By "predominantly" it is meant that between about 60 and about 100 percent of the length 66 of the shaping elastic members 60, more particularly between about 80 and about 100 percent of the length 66 of the shaping elastic members 60 is located rearward of the transverse axis 106.

In an embodiment of the female version of the absorbent article 10 it is desirable that the length 55 of the channels 50 be less to the length 66 of the shaping elastic members 60. By "less" as to the female version it is meant that the length 55 of the channel 50 is between about 50 and about 80 percent of the length 66 of the shaping elastic members 60. As a result, the length 55 of the channels 50 is generally smaller than the length 66 of the shaping elastic members 60.

In an embodiment of the female version of the absorbent article 10 the length 55 of the channels 50 can range from about 50 mm to about 300 mm and more particularly from about 120 mm to about 160 and still further from about 130 mm to about 140 mm. In an embodiment, the length of the shaping elastic members 60 can range from about 50 mm to about 300 mm, more particularly from about 200 mm to about 250 mm and still further from about 210 mm to about 230 mm.

In the unisex version, the shaping elastic members 60 are more centrally located about the transverse axis 106 of the absorbent article 10. As a result, it is desired that in this configuration, the outward, convex shape P of the absorbent core 40 is more pronounced in the central portion of the crotch region 23 to slightly forward of the crotch region 23 of the absorbent core 40 so as to be aligned with the target zone 122. To create this effect, the front end 62 and the rear end 64 of the shaping elastics members 60 are respectively rearward of the front ends 51 and rear ends 52 of the channels 50. By "rearward" it is meant that the respective element of the article 10 is closer to the rear waist edge 25*b*/chassis rear end edge than the other element.

In the embodiment of FIGS. 1C and 3C, the shaping elastics members 60 will be predominantly in the crotch region 23 of the article 10. By predominantly it is meant that the midpoint of the length 66 of the shaping elastic member 66 is offset from the transverse axis 106 by no more than about 5 to about 30 percent of the total length 66 of the shaping elastic member 60, more particularly, no more than about 5 to about 20 percent of the total length 66 of the shaping elastic member 60.

In an embodiment of the unisex version of the absorbent article 10 it is desirable that the length 55 of the channels 50 be less than the length 66 of the shaping elastic members 60. By "less" as to the unisex version it is meant that the length 55 of the channel 50 is between about 60 and about 90 percent of the length 66 of the shaping elastic members 60, more particularly, between about 70 and about 80 percent of the length 66 of the shaping elastic member 60.

In an embodiment of the unisex version of the absorbent article 10 the length 55 of the channels 50 can range from about 50 mm to about 300 mm and more particularly from about 120 mm to about 160 mm and still further from about 130 mm to about 140 mm. In an embodiment, the length of the shaping elastic members 60 can range from about 50 mm to about 400 mm and more particularly from about 150 mm to about 250 mm and still further from about 160 mm to about 200 mm.

To create the enhanced convex shape P of the absorbent article 10 according to the present invention, it was determined that the packing of the absorbent article 10 played an important part in the ability of the absorbent article 10 to take on the pronounced convex shape P once the product had been removed from its compressed configuration in the package. More particularly, it was discovered that the lateral and longitudinal folding of the absorbent article 10 in conjunction with the design, location and interaction of the proximal end 82 of the containment flaps 80, the location of the shaping elastic members 60 and the positioning of the channels 50 together played an important role in creating the enhanced convex configuration of the present invention.

FIG. 6 is cross-sectional end view along line 6-6 of FIG. 4A of the absorbent article 10 of FIG. 1A when in a folded state as it would look after it had been removed from a package of compressed absorbent articles, opened fully and then folded in half again generally along the transverse axis 106.

To create a configuration of an absorbent article 10 with a pronounced convex configuration using the embodiments of FIGS. 1A, 1B and 1C as well as other embodiments of the present invention, the absorbent article 10 is folded along a first fold line 140 (140*a* and 140*b*) on either side of the longitudinal axis 100 which is in alignment with the vertical line 130 shown in FIG. 5. The first fold lines 140*a* and 140*b* extend in a longitudinal direction 100. To make the first fold, the portion of the absorbent article 10 lying laterally outboard of both first fold lines 140 (140*a* and 140*b*) is folded inwardly over top of the topsheet 30 towards the longitudinal axis 100. As a result, the portions of the chassis 20 lying outboard of the fold line 140 including, in the embodiments illustrated, the respective side edges 24*a* and 24*b* as well as the leg elastics 70 (70*a*, 70*b*) are folded over top of the body facing surface 31 of the topsheet 30 as well as the chassis body facing surface 20*a* of the chassis 20. Furthermore, this first fold line 140 (one on either side of the article 10) is in line with the shaping elastic members 60 and the proximal ends 82 of the containment flaps 80 and thus line 130 as shown in FIG. 5 on either side of the article 10 and thus on either side of the longitudinal axis 100.

Once the first folds along the first fold lines 140*a* and 140*b* have been made, the absorbent article 10 is then folded in half transversely by a second fold line 142 which is substantially in line with the transverse axis 106. As a result of this second folding step, the front waist region 21 is folded over the rear waist region 22 such that the topsheet 30 in each region is adjacent one another and the front waist edge 25*a* is in substantial alignment with the rear waist edge 25*b*. The absorbent article 10, once in this configuration, is then ready for packaging and shipment.

The actual effect of this combination of elements and folding is shown in photographic form in FIGS. 7-9. FIG. 7A-1 is a photograph of a side perspective view of a male version of an absorbent article 10, having a construction as is shown in FIG. 1A, when in a folded state as it would look when first removed from a package of compressed absorbent articles according to the present invention. FIG. 7A-2 is a photograph of a side perspective view of a prior art conventional absorbent article when in a folded state as it would look when first removed from a package of compressed absorbent articles. This prior art product is lacking the shaping elastics 60 and its channels are centrally located generally about the lateral axis of the product. This prior art product is commercially available from Yuhan-Kimberly Ltd. of Seoul, South Korea under the trade designation HUGGIES PREMIER PLUS diaper. It is folded in the same manner as the absorbent article 10 shown in FIG. 7A-1.

In comparing the two products, the relative profile of each product is relatively similar to one another due to the compression forces of being packaged overriding the effects of the shaping elastics 66 and the overall interactive design of the absorbent article 10 according to the present invention.

FIG. 7B-1 is a photograph of a side perspective view of a male version of an absorbent article 10, having a construction as is shown in FIG. 1A, when in a folded state as it would look after it had been removed from a package of compressed absorbent articles, opened fully and then refolded showing the enhanced curvature P of the absorbent article 10 due to the activation and interaction of the variously-described components according to the present invention. FIG. 7B-2 is a photograph of a side perspective view of the prior art conventional absorbent article when in a folded state as it would look after it had been removed from a package of compressed absorbent articles, opened fully and then refolded.

In the unfolding step, the opposed front and rear waist edges 25*a* and 25*b* are opened up and the portions of the longitudinal sides edges 24 which have been folded over the topsheet body facing surface 31 of topsheet 30 are opened up and unfolded laterally outward away from the topsheet 30. By "opened fully" it is meant that the absorbent article has been grasped by hand in the vicinity of the front waist edge 25*a* and rear waist edge 25*b* and then stretched in opposite directions along the longitudinal direction 100 until the product is taught and then the product is allowed to relax. The absorbent article 10 is also grasped by hand in the front waist region 25*a* adjacent the longitudinal side edges 24*a* and 24*b* and pulled in the lateral direction 106 until the product is taught and then the product is allowed to relax. Finally, the same procedure is done in the rear waist region 25*b*. The absorbent article 10 is grasped by hand in the rear waist region 25*b* adjacent the longitudinal side edges 24*a* and 24*b* and pulled in the lateral direction 106 until the product is taught and then the product is allowed to relax. (These three stretching steps can be done in any order.) After the absorbent article 10 has been stretched in the above-described method, the absorbent article is refolded back into the configuration it had when removed from the compressed packaging. For the present invention, the longitudinal side edges 24 of the absorbent article 10 are folded back in over the topsheet 30 and the product is then folded in half along its lateral axis 106 which corresponds to the second fold line 142 such that the front waist edge 25*a* and the rear waist edge 25*b* are realigned with one another. No downward force is applied to the crotch region 23 or the front waist region 21 or the rear waist region 22 when refolding except for the force in pushing the front and rear waist edges 25*a* and 25*b* together. (This same folding and unfolding process is used with respect to the other embodiments of the absorbent article 10 shown in the remaining photographs in FIGS. 7C-1, 8B-1, 8C-1, 9B-1 and 9C-1. The prior art products are refolded into their original configuration in FIGS. 7B-2, 7C-2, 8B-2, 8C-2, 9B-2 and 9C-2 in the same manner. Again no downward force is applied to the crotch region or the front waist region or the rear waist region except for the force in pushing the front and rear waist edges together.)

In comparing the two products, it can be seen that the absorbent article 10 in FIG. 7B-1 has a much more pronounced convex curvature relative to the prior art product in FIG. 7B-2. The front waist panel 21 and the rear waist panel 22 as well as the crotch region 23 can be seen separated from one another. It is this enhanced convex curvature P that provides increased separation of the topsheet 30 and absorbent core 40 from the genitalia of wearer. As a result, there in increased air space between the topsheet 30 and the genital area of the wearer as the convex curvature P allows the absorbent article 10 to stand further away from the wearer. This is particularly advantageous when the article 10 has become soiled but body exudates such as urine, feces and menses.

FIG. 7C-1 is a photograph of an end perspective view of a male version of an absorbent article 10, having a construction as is shown in FIG. 1A, when in a folded state as it would look after it had been removed from a package of compressed absorbent articles, opened fully and then refolded showing the enhanced curvature P of the absorbent article 10 due to the activation and interaction of the variously-described components according to the present invention. FIG. 7C-2 is a photograph of an end perspective view of the prior art conventional absorbent article when in a folded state as it would look after it had been removed from a package of compressed absorbent articles, opened fully and then refolded. Again, this end view shows the greatly increased curvature P of the absorbent article 10 as compared to the prior art product. This same separation is illustrated in FIGS. 4A and 6.

Figures 1, 2, 8B:
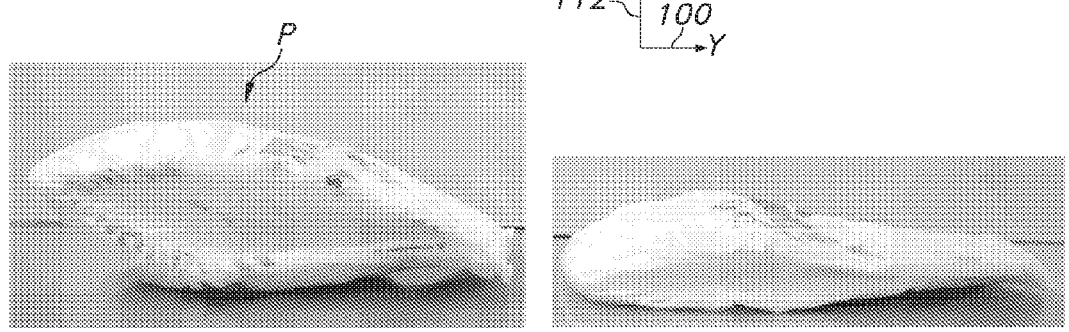
Figures 1, 2, 8C:
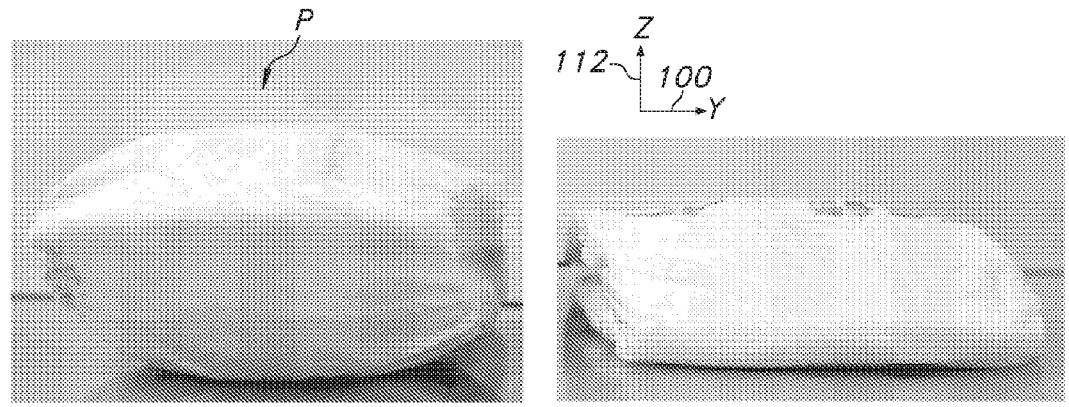

FIG. 8A-1 is a photograph of a side perspective view of a female version of an absorbent article 10, having a construction as is shown in FIG. 1B, when in a folded state as it would look when first removed from a package of compressed absorbent articles 10 according to the present invention. FIG. 8A-2 is a photograph of a side perspective view of the prior art conventional absorbent article when in a folded state as it would look when first removed from a package of compressed absorbent articles. FIG. 8B-1 is a photograph of a side perspective view of a female version of an absorbent article 10, having a construction as is shown in FIG. 1B, when in a folded state as it would look after it had been removed from a package of compressed absorbent articles, opened fully and then refolded showing the enhanced curvature P of the absorbent article 10 due to the activation and interaction of the variously-described components according to the present invention. FIG. 8B-2 is a photograph of a side perspective view of a prior art conventional absorbent article when in a folded state as it would look after it had been removed from a package of compressed absorbent articles, opened fully and then refolded. FIG. 8C-1 is a photograph of an end perspective view of a female version of an absorbent article 10, having a construction as is shown in FIG. 1B, when in a folded state as it would look after it had been removed from a package of compressed absorbent articles, opened fully and then refolded showing the enhanced curvature P of the absorbent article 10 due to the activation and interaction of the variously-described components according to the present invention. FIG. 8C-2 is a photograph of an end perspective view of the prior art conventional absorbent article when in a folded state as it would look after it had been removed from a package of compressed absorbent articles, opened fully and then refolded. Once again for the female version of an absorbent article 10 as compared to the conventional prior art product, there is a much more pronounced convex curvature P of the absorbent article 10 according to the present invention.

FIG. 9A-1 is a photograph of a side perspective view of a unisex version of an absorbent article 10, having a construction as is shown in FIG. 1C, when in a folded state as it would look when first removed from a package of compressed absorbent articles 10 according to the present invention. FIG. 9A-2 is a photograph of a side perspective view of the prior art conventional absorbent article when in a folded state as it would look when first removed from a package of compressed absorbent articles. FIG. 9B-1 is a photograph of a side perspective view of a unisex version of an absorbent article 10, having a construction as is shown in FIG. 1C, when in a folded state as it would look after it had been removed from a package of compressed absorbent articles, opened fully and then refolded showing the enhanced curvature P of the absorbent article 10 due to the activation and interaction of the variously-described components according to the present invention. FIG. 9B-2 is a photograph of a side perspective view of the prior art conventional absorbent article when in a folded state as it would look after it had been removed from a package of compressed absorbent articles, opened fully and then refolded. FIG. 9C-1 is a photograph of an end perspective view of a unisex version of an absorbent article 10, having a construction as is shown in FIG. 1C, when in a folded state as it would look after it had been removed from a package of compressed absorbent articles, opened fully and then refolded showing the enhanced curvature P of the absorbent article 10 due to the activation and interaction of the variously-described components according to the present invention. FIG. 9C-2 is a photograph of an end perspective view of the prior art conventional absorbent article when in a folded state as it would look after it had been removed from a package of compressed absorbent articles, opened fully and then refolded. Once again for the unisex version of an absorbent article 10 as compared to the conventional prior art product, there is a much more pronounced convex curvature P of the absorbent article 10 according to the present invention.

As stated at the outset, the present invention can be employed in many applications with respect to personal care absorbent articles, not just open diapers but closed and/or refastenable products as well for use with babies, small children and adults. It also can be used with respect to feminine hygiene products. FIGS. 10 and 11 depict a training pant 10 as has been previously described and discussed herein. It can be either a fixed-side product with sealed seams 91 or it can be fitted with refastenable members such as the mechanical hook and loop fasteners employed with the open diaper. In both configurations, it too can be assembled and folded prior to packaging in the same fashion as the open diaper depicted in FIGS. 1-9 thereby resulting in the pronounced convex curvature P displayed with the other embodiments.

The method of forming such an absorbent article 10 according to the present invention involves positioning an absorbent core 40 between a liquid pervious topsheet 30 and a liquid impervious backsheet 32 to form a chassis 20. The chassis 20 defines a longitudinal axis 100, a transverse axis 106 and a vertical z-directional axis 112 orthogonal to the longitudinal and transverse axes 100, 106. The chassis 20 has a front waist region 21 and a rear waist region 22 separated by a crotch region 23 with the chassis 20 having opposed chassis transverse end edges 25 and opposed chassis longitudinal side edges 24. The absorbent core 40 has opposed transverse absorbent core end edges 42, opposed longitudinal absorbent core side edges 41 including a left side edge 41a and a right side edge 41b, and an absorbent core thickness 43.

At least one and preferably a plurality of channels 50 are created in the absorbent core 40 extending through the absorbent core thickness 43. In an embodiment, the channels are located in the crotch region 43 and the front waist region 21 of the chassis 20.

A pair of containment flaps 80 are attached to the chassis 20 with each of the pair of containment flaps 80 having a proximal end 82 and a distal end 84. The proximal end 82 of each of the pair of containment flaps 80 is attached to the chassis 20 in at least the crotch region 23 and extends in the direction of the longitudinal axis 100. The proximal end 82a of one of the pair of containment flaps 80 is located outboard of the left side edge 41a of the absorbent core 40 and the proximal end 82*b* of the other of the pair of containment flaps 80 is located outboard of the right side edge 41*b* of the absorbent core 40.

A pair of leg elastic members 70 are attached to the chassis 20 with one each of the pair of leg elastic members (left leg elastic member 70*a* and right leg elastic member 70*b*) being positioned adjacent a respective opposite chassis side edge 24 (24*a*, 24*b*) in the crotch region 23 of the article 10 on opposite sides of the longitudinal axis 100 transversely outboard of the shaping elastic members 60.

A pair of shaping elastic members 60 (60*a*, 60*b*) are attached to the chassis 20 extending in the direction of the longitudinal axis 100 with one of the pair of shaping elastic members 60*a* being located outboard of the left side edge 41*a* of the absorbent core 40 and the other of the pair of shaping elastic members 60*b* being located outboard of the right side edge 41*b* of the absorbent core 40. The locating is done such that each of the pair of shaping elastic members 60*a*, 60*b* is in vertical juxtaposition (see line 130 in FIG. 5 which corresponds with fold lines 140*a* and 140*b* in FIG. 1) with respect to the proximal end 82*a*, 82*b* of a respective one of the pair of containment flaps 80 (80*a*, 80*b*) relative to the direction of the z-directional axis 112 in the crotch region 23. This location also results in the respective shaping elastic members 60*a* and 60*b* being inboard of the respective leg elastic members 70*a* and 70*b* in the transverse direction of the product. In an embodiment, the backsheet can be formed of a body facing layer 34 and a garment facing layer 36 and the pair of shaping elastic members 60 can be attached to the chassis 20 between the body facing layer 34 and the garment facing layer 36. When the backsheet 32 is a single layer, the shaping elastic members 60 can be attached to the body facing side of the backsheet 32 or to other layers and components of the absorbent article 10. It is desirable, however, that the shaping elastic members 60 be located outside of any core wrap material 57 as the elastic forces created by the members 60 could possibly tear the core wrap 57 whether the absorbent article 10 be a diaper, a training pant or another of the articles described herein.

After the absorbent article 10 is formed, it is folded along a first fold line 140 (140*a*, 140*b*) (see FIGS. 1-3) outboard of a respective longitudinal absorbent core side edge (41*a*, 41*b*) of the absorbent core 40. Each of the first fold lines 140*a*, 140*b* extends in the direction of the longitudinal axis 100 with each of the first fold lines 140*a*, 140*b* being in vertical juxtaposition relative to the Z-directional axis 112 with the respective proximal edges 82 (82*a*, 82*b*) of the containment flaps 80 (80*a*, 80*b*) and the respective shaping elastic members 60 (60*a*, 60*b*) on either side of the product. The folding causes the respective leg elastic members 70 (70*a*, 70*b*) to be folded inwardly over a body-facing side 44 of the absorbent core 40 and the body facing surface 31 of the topsheet 30 and the chassis body facing surface 20*a* of the chassis 20. Finally the article 10 is folded in the crotch region 23 along a transverse second fold line 142 in the direction of the transverse axis 106. In an embodiment, the transverse second fold line 142 extends through the channels 50 and shaping elastic members 60. In an embodiment, the plurality of channels 50 are created more towards the from waist region 21 than the rear waist region 22.

Once the absorbent article 10 is configured and folded in this format, it can be packaged in a compressed multi-pack of absorbent articles using conventional packaging equipment. After removal from the package, the consumer opens the absorbent article and unfolds it, typically by grabbing one or more of the edges of the product and stretching it open as previously described in the longitudinal and lateral directions. Due to the unique combination and interaction of elements, including the channels 50 and the shaping elastic members 60, the containment flaps 80 and their proximal ends 82, as well as the location of the fold lines 140 and 142 relative to the described elements, the article 10 according to the present invention will take on a more pronounce convex configuration P as compared to conventional products such that the topsheet 30 is curved outwardly away from the wearer thereby creating an air space between the wearer and the product in the area of convex curvature P. Depending on the location of the channels 50 and shaping elastic members 60, embodiments can be created which are specifically tailored to conform to the male and female genitalia. For males, this means that this exaggerated outward curvature P will be located in the area of the penis and thus more towards the forward portion of the crotch region 23 and into the front waist region 21 of the product to coincide with the male insult area 120. For the female, this exaggerated outward curvature P will be located in the area of the vagina and thus closer to the crotch region 23 of the product to coincide with the female insult area 121. If a unisex design is desired, this exaggerated outward curvature will be located at a midpoint between the ideal locations for the male and female configurations to coincide with the unisex insult area 122.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a chassis having a liquid-permeable topsheet, a liquid-impermeable backsheet and an absorbent core located between said topsheet and said backsheet, said chassis defining a longitudinal axis, a transverse axis and a z-directional axis orthogonal to said longitudinal and transverse axes, said chassis having a front waist region and a rear waist region separated by a crotch region, said chassis having opposed chassis end edges including a chassis front end edge and a chassis rear end edge and opposed chassis side edges, said absorbent core having opposed transverse absorbent core end edges, opposed longitudinal absorbent core side edges including a left side edge and a right side edge, and an absorbent core thickness, said absorbent core defining a plurality of channels therein extending through said absorbent core thickness, said channels being located in said crotch region and said front waist region of said chassis, a pair of containment flaps each having proximal end and a distal end, said proximal end of each of said pair of containment flaps being attached to said chassis in at least said crotch region and extending in the direction of said longitudinal axis, said proximal end of one of said pair of containment flaps being located outboard of said left side edge of said absorbent core and said proximal end of the other of said pair of containment flaps being located outboard of said right side edge of said absorbent core, a pair of leg elastic members attached to said chassis, one each of said pair of leg elastic members being positioned adjacent a respective chassis side edge in said crotch region of said article on opposite sides of said longitudinal axis, a pair of shaping elastic members extending in the direction of said longitudinal axis, one of said pair of shaping elastic members being located outboard of said left side edge of said absorbent core and the other of said pair of shaping elastic members being located outboard of said right side edge of said absorbent core, each of said pair of shaping elastic members being in vertical juxtaposition with respect to said proximal end of a respective one of said pair of containment flaps relative to the direction of said z-directional axis in said crotch region and applying a tensile force to the absorbent article lower than the tensile forces applied to the absorbent article by the pair of leg elastic members, said pair of shaping elastic members causing said chassis to have a convex shape in at least a portion of said front waist region or said crotch region.

2. The absorbent article of claim 1 wherein said plurality of channels are located in said crotch region and said front waist region of said chassis.

3. The absorbent article of claim 1 wherein said plurality of channels are positioned more towards said front waist region and said chassis front end edge than said rear waist region.

4. The absorbent article of claim 1 wherein said shaping elastics have a length and said channels in said absorbent core define a length, said length of said shaping elastic members being generally equal to said length of said channels in said absorbent core.

5. The absorbent article of claim 1 wherein said shaping elastics have a length and said channels in said absorbent core define a length, said length of said shaping elastics being longer than said length of said channels in said absorbent core.

6. An absorbent article comprising a chassis having a liquid-permeable topsheet, a liquid-impermeable backsheet and an absorbent core located between said topsheet and said backsheet, said chassis defining a longitudinal axis, a transverse axis and a z-directional axis orthogonal to said longitudinal and transverse axes, said chassis having a front waist region and a rear waist region separated by a crotch region, said chassis having opposed chassis end edges including a chassis front end edge and a chassis rear end edge and opposed chassis side edges, said absorbent core having opposed transverse absorbent core end edges, opposed longitudinal absorbent core side edges including a left side edge and a right side edge, and an absorbent core thickness, said absorbent core defining a plurality of channels therein extending through said absorbent core thickness, a pair of containment flaps each having proximal end and a distal end, said proximal end of each of said pair of containment flaps being attached to said chassis in at least said crotch region and extending in the direction of said longitudinal axis, said proximal end of one of said pair of containment flaps being located outboard of said left side edge of said absorbent core and said proximal end of the other of said pair of containment flaps being located outboard of said right side edge of said absorbent core, a pair of leg elastic members attached to said chassis, one each of said pair of leg elastic members being positioned adjacent a respective chassis side edge in said crotch region of said article on opposite sides of said longitudinal axis, a pair of shaping elastic members extending in the direction of said longitudinal axis, one of said pair of shaping elastic members being located outboard of said left side edge of said absorbent core and the other of said pair of shaping elastic members being located outboard of said right side edge of said absorbent core, each of said pair of shaping elastic members being in vertical juxtaposition with respect to said proximal end of a respective one of said pair of containment flaps relative to the direction of said z-directional axis in said crotch region and applying a tensile force to the absorbent article lower than the tensile forces applied to the absorbent article by the pair of leg elastic members, said pair of shaping elastic members causing said chassis to have a convex shape in at least a portion of said front waist region or said crotch region, said article being folded prior to wearing along a first fold line on each side of said absorbent core outboard of a respective longitudinal absorbent core side edge of said absorbent core, each said first fold line extending in the direction of said longitudinal axis, each said first fold line being in vertical juxtaposition relative to the Z-directional axis with said respective shaping elastic members and said proximal ends of said containment flaps in said crotch region, said folding causing said respective leg elastic members to be folded inwardly over a body-facing side of said absorbent core, said article being further folded in said crotch region prior to wearing along a transverse second fold line in the direction of said transverse axis.

7. The absorbent article of claim 6 wherein said transverse second fold line extends through said channels and shaping elastic members.

8. The absorbent article of claim 6 wherein said backsheet has a body facing layer and a garment facing layer, said shaping elastic members being located between said body facing layer and said garment facing layer of said backsheet.

9. The absorbent article of claim 6 wherein said shaping elastic members are located predominantly in said crotch region and said front waist region of said chassis.

10. The absorbent article of claim 9 wherein said channels are each defined by a front end and a rear end, and said shaping elastic members each have a front end and a rear end, said front end and said rear end of said shaping elastic members being respectively forward of said front end and said rear end of said channels and therefore closer to said chassis front end edge than said front end and said rear end of said channels.

11. The absorbent article of claim 6 wherein said shaping elastic members are located predominantly in said crotch region and said rear waist region of said chassis.

12. The absorbent article of claim 11 wherein said channels are each defined by a front end and a rear end, and said shaping elastics each have a front end and a rear end, said front end and said rear end of said shaping elastic members being respectively rearward of said front end and said rear end of said channels and therefore closer to said chassis rear end edge than said front end and said rear end of said channels.

13. The absorbent article of claim 6 wherein said shaping elastics are located predominately in said crotch region of said chassis.

14. The absorbent article of claim 13 wherein said channels are each defined by a front end and a rear end, and said shaping elastic members each have a front end and a rear end, said front end and said rear end of said shaping elastic members being respectively rearward of said front end and said rear end of said channels and therefore closer to said chassis rear end edge than said front end and said rear end of said channels.

15. The absorbent article of claim 6 wherein said plurality of channels are located in said crotch region and said front waist region of said chassis.

16. The absorbent article of claim 6 wherein said plurality of channels are positioned more towards said front waist region and said chassis front end edge than said rear waist region.

17. A method of creating and folding an absorbent article comprising:
   positioning an absorbent core between a liquid pervious topsheet and a liquid impervious backsheet to form a chassis, said chassis defining a longitudinal axis, a transverse axis and a z-directional axis orthogonal to said longitudinal and transverse axes, said chassis having a front waist region and a rear waist region separated by a crotch region, said chassis having opposed chassis end edges including a chassis front end edge and a chassis rear end edge and opposed chassis side edges, said absorbent core having opposed transverse absorbent core end edges, opposed longitudinal absorbent core side edges including a left side edge and a right side edge, and an absorbent core thickness,
   creating a plurality of channels in said absorbent core extending through said absorbent core thickness, said channels being located in said crotch region and said front waist region of said chassis,
   attaching a pair of containment flaps to said chassis, each of said pair of containment flaps having a proximal end and a distal end, said proximal end of each of said pair of containment flaps being attached to said chassis in at least said crotch region and extending in the direction of said longitudinal axis, said proximal end of one of said pair of containment flaps being located outboard of said left side edge of said absorbent core and said proximal end of the other of said pair of containment flaps being located outboard of said right side edge of said absorbent core,
   attaching a pair of leg elastic members to said chassis, one of said pair on either side of said longitudinal axis adjacent a respective chassis side edge,
   attaching a pair of shaping elastic members to said chassis extending in the direction of said longitudinal axis, one of said pair of shaping elastic members being located outboard of said left side edge of said absorbent core and the other of said pair of shaping elastic members being located outboard of said right side edge of said absorbent core, each of said pair of shaping elastic members being attached to said chassis to apply a tensile force to the chassis that is lower than tensile forces applied to the chassis by said pair of leg elastic members,
   locating each of said pair of shaping elastic members in vertical juxtaposition with respect to said proximal end of a respective one of said pair of containment flaps relative to the direction of said z-directional axis in said crotch region,
   folding said article along a first fold line on each side of said absorbent core outboard of a respective longitudinal absorbent core side edge of said absorbent core, each said first fold line extending in the direction of said longitudinal axis, each said first fold line being in vertical juxtaposition relative to the Z-directional axis with one of said respective shaping elastic members and said proximal ends of said containment flaps, said folding causing said respective leg elastic members to be folded inwardly over a body-facing side of said absorbent core, and
   folding said article in said crotch region along a transverse second fold line in the direction of said transverse axis.

18. The method of claim 17 wherein said transverse second fold line extends through said channels and shaping elastic members.

19. The method of claim 18 wherein said backsheet has a body facing layer and garment facing layer and said shaping elastic members are located between said body facing layer and said garment facing layer.

20. The method of claim 17 wherein said plurality of channels are created more towards said front waist region than said rear waist region and therefore closer to said chassis front end edge than said chassis rear end edge.

* * * * *